US006541520B1

(12) United States Patent
Dewey et al.

(10) Patent No.: US 6,541,520 B1
(45) Date of Patent: *Apr. 1, 2003

(54) TREATMENT OF ADDICTION AND ADDICTION-RELATED BEHAVIOR

(75) Inventors: Stephen L. Dewey, Manorville, NY (US); Jonathan D. Brodie, Cos Cob, CT (US); Charles R. Ashby, Jr., Miller Place, NY (US)

(73) Assignee: Brookhaven Science Associates, Upton, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/209,952

(22) Filed: Dec. 11, 1998

Related U.S. Application Data

(63) Continuation-in-part of application No. 09/189,166, filed on Nov. 9, 1998, which is a continuation-in-part of application No. 09/129,253, filed on Aug. 5, 1998, now Pat. No. 6,057,368.

(51) Int. Cl.$^7$ .......................... A01N 37/12; A01N 33/24

(52) U.S. Cl. ....................... 514/561; 514/810; 514/811; 514/812; 514/813; 514/291; 514/304; 514/332; 514/343; 514/357; 514/640; 514/641

(58) Field of Search .................. 514/291, 810–812, 514/561, 304, 332, 343, 357, 640, 641, 813, 811; 424/408, 464, 484

(56) References Cited

U.S. PATENT DOCUMENTS

| | | |
|---|---|---|
| 3,639,607 A | 2/1972 | Phillips |
| 4,540,582 A | 9/1985 | Seiler et al. ................. 514/561 |
| 4,595,697 A | 6/1986 | Seiler et al. ................. 514/534 |
| 4,621,145 A | 11/1986 | Frieben et al. ............... 548/543 |
| 5,189,064 A | * 2/1993 | Blum et al. .................. 514/561 |
| 5,760,049 A | * 6/1998 | Viner .......................... 514/291 |
| 5,824,684 A | * 10/1998 | Viner .......................... 514/291 |

FOREIGN PATENT DOCUMENTS

WO    WO 89 03211 A    4/1989

OTHER PUBLICATIONS

Morgan et al., "Longterm Cocaine Administration May Alter Specific Gabergic Pathways", *Abstracts Society for Neuroscience*, 23:1942 (1997).
Kushner et al., "Comparison of the Effects of Vigabatrin on Cocaine Self–Administration and Food Reinforcement", *Abstracts Society for Neuroscience*, 23:1942 (1997).
Dewey et al., "GABAergic Attenuation of Cocaine–Induced Dopamine Release and Locomotor Activity", *Synapse*, 25:393–398 (1997).
Morgan et al., "Effects of Pharmacologic Increases Brain GABA Levels on Cocaine–Induced Changes in Extracellular Dopamine", *Synapse* 28:60–65 (1998).
Kushner et al., "Gamma–vinyl GABA Attenuates Cocaine–Induced Lowering of Brain Stimulation Reward Thresholds", *Physiopharmacology* 133:383–388 (1997).
Porter et al., "Antiepileptic Drugs", *Basic and Clinical Pharmacology*, ed. by Katzung, B.G., Appelton and Lange, Stamford, CT pp. 386–408 (1998).
Takada et al., "Drug Dependence Study on Vigabatrin in Rhesus Monkeys and Rats", *Arzneim.–Forsch.'Drug Res* 47(II), 1087–1092 (1997).
Nisell et al., "Nicotine Dependence, Midbrain Dopamine Systems and Psychiatric Disorders", *Pharmacology & Toxicology* 76:157–162 (1995).
Nisell et al., "Infusion of Nicotine in the Ventral Tegmental Area or the Nucleus Accumbens of the Rat Differentially Affects Accumbal Dopamine Release", *Pharmacology & Toxicology*, 75:348–352 (1994).
Fudala et al., "Pharmacologic Characterization of Nicotine–Induced Conditioned Place Preference", *Pharmacol Biochem Behav* 22(2) 237–241 (1985).
Clarke et al., "Apparent Absence of Nicotine–Induced Conditioned Place Preference in Rats" *Psychopharmacology*, 92: 84–88 (1987).
Clarke et al., "Evidence That Mesolimbic Dopaminergic Activation Underlies the Locomotor Stimulant Action of Nicotine in Rats", *The Journal of Pharmacology and Experimental Therapeutics*, 246:701–708 (1988).
Henningfield et al., "Control of Behavior by Intravenous Nicotine Injections in Human Subjects", *Pharmacology Biochemistry & Behavior* 19:1021–1026 (1983).
Jarvik et al., "Pharmacological Treatment of Tobacco Dependance", *Pharmacology Biochemistry & Behavior* 30:279–294 (1988).
Henningfield et al., "Cigarette Smokers Self–Administer Intravenous Nicotine", *Pharmacology Biochemistry & Behavior* 19:887–890 (1983).

(List continued on next page.)

Primary Examiner—Padmashri Ponnaluri
(74) Attorney, Agent, or Firm—Margaret C. Bogosian

(57) ABSTRACT

The present invention provides a highly efficient method for treating substance addiction and for changing addiction-related behavior of a mammal suffering from substance addiction. The method includes administering to a mammal an effective amount of gamma vinylGABA or a pharmaceutically acceptable salt thereof. The present invention also provides a method of treatment of cocaine, morphine, heroin, nicotine, amphetamine, methamphetamine, or ethanol addiction by treating a mammal with an effective amount of gamma vinylGABA or a pharmaceutically acceptable salt thereof. In one embodiment, the method of the present invention includes administering to the mammal an effective amount of a composition which increases central nervous system GABA levels wherein the effective amount is sufficient to diminish, inhibit or eliminate behavior associated with craving or use of drugs of abuse. The composition includes GVG, gabapentin, valproic acid, progabide, gamma-hydroxybutyric acid, fengabine, cetylGABA, topiramate or tiagabine or a pharmaceutically acceptable salt thereof, or an enantiomer or a racemic mixture thereof.

31 Claims, 9 Drawing Sheets

OTHER PUBLICATIONS

Nisell et al., "Systemic Nicotine–Induced Dopamine Release in the Rat Nucleus Accumbens is Regulated by Nicotinic Receptors in the Ventral Tegmental Area", *Synapse* 16:36–44 (1994).

Pontieri et al., "Effects of nicotine on the nucleus accumbens and similarity to those of addictive drugs" *Nature* 382:255–257 (1996).

Di Chiara et al., "Drugs Abused by Humans Preferentially Increase Synaptic Dopamine Concentrations in the Mesolimbic System of Freely Moving Rats", *Proc. Natl. Acad. Sci. USA*, 85:5274–5278 (1988).

Damsma et al., "Lack of Tolerance to Nicotine–Induced Dopamine Release in the Nucleus Accumbens", *European Journal of Pharmacology*, 168:363–368 (1989).

Imperato et al., "Nicotine Preferentially Stimulates Dopamine Release in the Limbic System of Freely Moving Rats" *European Journal of Pharmacology*, 132:337–338 (1986).

Brazell et al., "Acute Administration of Nicotine Increases the In Vivo Extracellular Levels of Dopamine, 3,4–Dihydroxyphenylacetic Acid and Ascorbic Acid Preferentially in the Nucleus Accumbens of the Rat: Comparison wth Caudate–Putamen", *Neuropharmacology* 29:1177–1185 (1990).

Horan et al., "Nicotine Produces Conditioned Place Preference in Lewis But Not Fischer 344 Rats", *Synapse* 26:93–94 (1997).

Lepore et al., "Conditioned Place Preference Induced by $\Delta^9$ – Tetrahydrocannibinol: Comparison with Cocaine, Morphine, and Food Reward", *Life Sciences*, 56:2073–2080 (1995).

Sora et al., "Cocaine reward models: conditioned place preference can be established in dopamine– and in serotonin– transporter knockout mice" *Proc. Natl. Acad. Sci. USA* 95:7699–7704 (1998).

Valentine et al., "Self–Administration in Rats Allowed Unlimited Access to Nicotine" *Psychopharmacology*, 133:300–305 (1997).

Eliot L. Gardner, "6 Brain Reward Mechanisms", *Substance Abuse: A Comprehensive Textbook*, pp.51–85 (1997).

Marshall et al., "Prestnaptic Nicotinic Modulation of Dopamine Release in the Three Ascending Pathways Studied by In Vivo Microdialysis: Comparison of Naive and Chronic Nicotine–Treated Rats" *Journal of Neurochemistry*, 68:1511–1519 (1997).

M.–F. Chesselet, "Presynaptic Regulation of Neurotransmitter Release in the Brain", *Neuroscience* 12:347–375 (1984).

Lacey et al., "On the Potassium Conductance Increase Activated by $GABA_B$ and Dopamine $D_2$ Receptors in Rat Substantia Nigra Neurones" *Journal of Physiology* 401:437–453 (1988).

Grant et al., "Vigabatrin: A Review of its Pharmacodynamic and Pharmacokinetic Properties, and Therapeutic Potential in Epilepsy and Disorders of Motor Control" *Durgs* 41 6:889–926 (1991).

Jung et al., "Vinyl GABA (4–amino–hex–5–enoic acid. A New Selective Irreversible Inhibitor of GABA–T: Effects on Brain GABA Metabolism in Mice," *Neurochem.* 29:797–802 (1977).

Tsuji et al., "Activation of Ventral Tegmental $GABA_B$ Receptors Inhibits Morphine–Induced Place Preference in Rats" *European Journal of Pharmacology* 313:169–173.

Roberts et al., "Baclofen Suppresion of Cocaine Self–Administration: Demonstration Using a Discrete Trials Procedure" *Psychopharmacology* 131:271–277 (1997).

Bolser et al., "The Pharmacology of SCH 50911: A Novel, Orally–Active GABA–B Receptor Antagonist" *The Journal of Pharmacology and Experimental Therapeutics* 274:1393–1398 (1995).

Roberts et al., "Baclofen Attenuates the Reinforcing Effects of Cocaine in Rats" *Neuropsychopharmacology* 15:417–423 (1996).

Derek van der Kooy, "Place Conditioning: A Simple and Effective Method for Assessing the Motivational Properties of Drugs" M.A. Bozarth Ed., Springer–Verlag, New York, pp. 229–241 (1987).

Hurt et al., "A Comparison of Sustained–Release Bupropion and Placebo for Smoking Cessation" *The New England Journal of Medicine* 337:1195:1202 (1997).

Volkow et al., "Imaging Endogenous Dopamine Competition With [$^{11}$C] Raclopride in the Human Brain" *Synapse* 16:255–262 (1994).

Logan et al., "Graphical Analysis of Reversible Radioligand Binding from Time–Activity Measurements Applied to [N–$^{11}$C–methyl]–(–)–Cocaine PET Studies in Human Subjects" *Journal of Cerebral Blood Flow and Metabolism* 10:740–747 (1990).

Dewey et al., "A Novel Strategy for the Treatment of Cocaine Addiction" *Synapse* 30:119–129 (1998).

Dewey et al., "Striatal Binding of the PET Ligand $^{11}$C–Raclopride is Altered by Drugs that Modify Synaptix Dopamine Levels" *Synapse* 13:350–356 (1993).

Dewey et al. "GABAergic Inhibition of endogeneous Dopamine Release Measured in vivo with $^{11}$C–Raclopride and Positron Emission Tomography" *The Journal of Neuroscience* 12(10):3773–3780 (1992).

Dewey et al., "Effects of Central Cholinergic Blockade on Striatal Dopamine Release Measured with Positron Emission Tomography in Normal Human Subjects" *Proc. Natl. Acad. Sci. USA* 90:11816–11820 (1993).

Buckland et al., "Amphetamine and Vigabatrin Down Regulate Aromatic L–amino acid Decarboxylase mRNA levels " *Molecular Brain Research* 35:69–76 (1996).

Cubells et al., "In Vivo Action of Enzyme–Activated Irreversible Inhibitors of Glutamic Acid Decarboxylase and γ–Aminobutyric Acid Transaminase in Retina vs. Brain" *The Journal of Pharmacology and Experimental Therapeutics* 238:508–514 (1986).

Herbert D. Kleber, "Treatment of Cocaine Abuse: Pharmacotherapy" *Cocaine Scientific and Social Dimensions* pp.195–206 (1992).

Ritz et al., "Psychostimulant Drugs and a Dopamine Hypothesis Regarding Addiction: Update on recent research" *Biochem. Soc. Symp.* 59:51–64.

Sherif et al., "Basic Aspects of GABA–transmission in Alcoholism, with Particular Reference to GABA–transaminase" *European Neuropsychopharmacology* 7:1–7(1997).

Dewey, et al., "A New GABAergic Stategy for Treating Cocaine Addiction", J. Nuclear Med., 39:5 suppl., pp. 99–100 (1998).

Morgan, et al., "Vigabatrin Attenuates Cocaine–Induces Changes in Brain Dopamine Concentrations", J. Nuclear Med., 38:5 suppl., p. 11p (1997).

* cited by examiner

Comparison of cocaine's effects on the DV ratio in group 1, 2, and 3, animals.
Each data point is derived from the calculation:

$$\frac{(DVSTscan1)}{(DVCB\ scan2)} / \frac{(DVSTscan2)}{(DVCBscan2)}$$

Individual points are shown for each study (n=20).

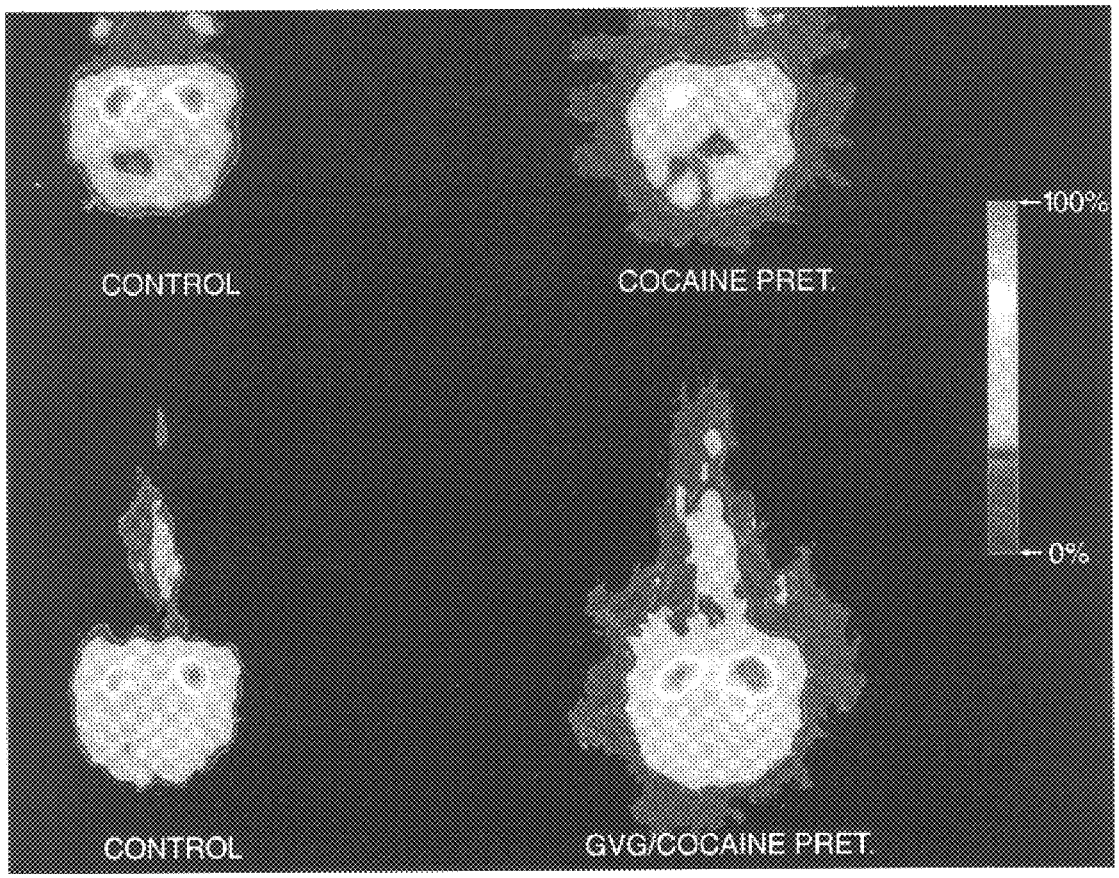

Transaxial parametric DV ratio images of the non-human primate brain as the level of the corpus striatum. The color scale indicates intensity of receptor availability (red indicates higher availability vs. magenta indicating a lower receptor availability). Cocaine decreases receptor availability (top right) compared to baseline values (top left). When pretreated with GVG, however, cocaine did not alter receptor availability (lower right) compared to baseline values (lower left).

FIGURE 2

Effects of GVG (150 mg/kg) on locomotor behavior compared with saline controls (open circles are GVG pretreated animals, closed circles are saline controls).

Effects of GVG (300 mg/kg) on locomotor behavior compared with saline controls (open circles are GVG pretreated animals, closed circles are saline controls).

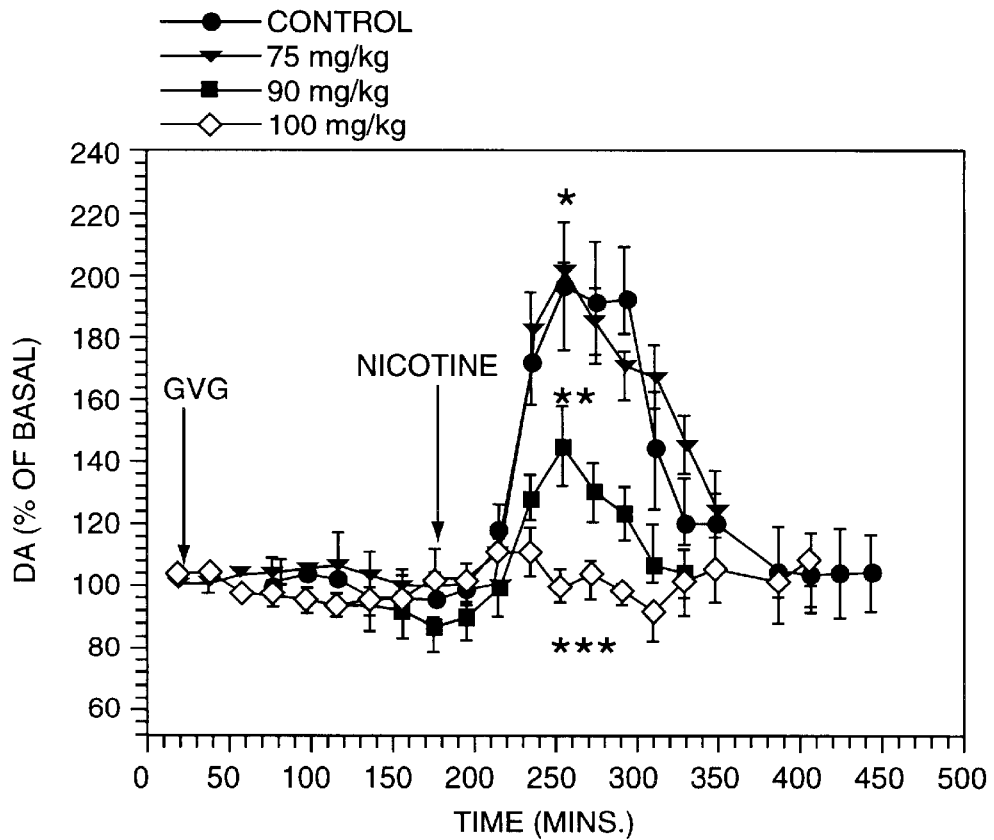

Effect of (-)-nicotine on extracellular NACC DA in naive freely moving rats.
* Values obtained following GVG (75 mg/kg) are not statistically different than normal controls (ANOVA and Student Neuman-Keuls test, p>.1).
 Values are statistically different (p<0.01) from control values (ANOVA and Student Neuman-Keuls test). * Values are statistically different (p<0.01) from control values (ANOVA and Student Neuman-Keuls test).

FIGURE 5a

Effect of (-)-nicotine on extracellular NACC DA in chronically treated freely moving rats.
* Values obtained following nicotine challenge in nicotine-treated animals and animals that received GVG (100 mg/kg) 24 hours prior to a nicotine challenge are not statistically different than normal control values (ANOVA and Student Neuman-Keuls test).

EFFECTS OF GVG ON METHAMPHETAMINE INDUCED
CHANGES IN DA IN NUC. ACC.

EFFECTS OF GVG ON ALCOHOL-INDUCED INCREASES IN NAc DA

TREATMENT OF ADDICTION AND ADDICTION-RELATED BEHAVIOR

The present application is a continuation-in-part of co-pending cation Ser. No. 09/189,166 filed on Nov. 9, 1998, which is a continuation-in-part of co-pending application Ser. No. 09/129,253 filed on Aug. 5, 1998, now U.S. Pat. No. 6,057,368 issued May 2, 2000.

This invention was made with Government support under Contract NO. DE-ACO2-98CH10886, between the U.S. Department of Energy and Brookhaven Science Associates and also under Contract Nos. NIMH MH49165, NIMH R2955155 between National Institutes of Mental Health and Brookhaven Science Associates. The Government has certain rights in the invention.

BACKGROUND OF THE INVENTION

This invention relates to the use of an irreversible inhibitor of GABA-transaminase for the treatment of substance addiction and modification of behavior associated with substance addiction. Substance addiction, such as drug abuse, and the resulting addiction-related behavior are enormous social and economic problems that continue to grow with devastating consequences.

Substance addiction can occur by use of legal and illegal substances. Nicotine, cocaine, amphetamine, methamphetamine, ethanol, heroin, morphine and other addictive substances are readily available and routinely used by large segments of the United States population.

Many drugs of abuse are naturally occurring. For example, cocaine is a naturally occurring nonamphetamine stimulant derived from the leaves of the coca plant, *Erythroylon coca*. Coca leaves contain only about one-half of one percent pure cocaine alkaloid. When chewed, only relatively modest amounts of cocaine are liberated, and gastrointestinal absorption is slow. Certainly, this explains why the practice of chewing coca leaves has never been a public health problem in Latin America. The situation changes sharply with the abuse of the alkaloid itself.

It has been found that addicting drugs such as nicotine, cocaine, amphetamine, methamphetamine, ethanol, heroin, and morphine enhance (in some cases directly, in other cases indirectly or even trans-synaptically) dopamine (DA) within the mesotelencephalic reward/reinforcement circuitry of the forebrain, presumably producing the enhanced brain reward that constitutes the drug user's "high." Alterations in the function of these DA systems have also been implicated in drug craving and in relapse to the drug-taking habit in recovering addicts. For example, cocaine acts on these DA systems by binding to the dopamine transporter (DAT) and preventing DA reuptake into the presynaptic terminal.

There is considerable evidence that nicotine, cocaine, amphetamine, methamphetamine, ethanol, heroin, morphine and other abused drugs' addictive liability is linked to reuptake blockade in central nervous system (CNS) reward/reinforcement pathways. For example, cocaine-induced increases in extracellular DA have been linked to its rewarding and craving effects in rodents. In humans, the pharmacokinetics binding profile of $^{11}$C-cocaine indicates that the uptake of labeled cocaine is directly correlated with the self-reported "high". In addition, human cocaine addicts exposed to cocaine-associated environmental cues experienced increased cocaine craving which is antagonized by the DA receptor antagonist haloperidol. Based upon the presumptive link between cocaine's addictive liability and the DA reward/reinforcement circuitry of the forebrain, many pharmacologic strategies for treating cocaine addiction have been proposed.

In the past, one treatment strategy was to target directly the DAT with a high-affinity cocaine analog, thereby blocking cocaine's binding. Another treatment strategy was to modulate synaptic DA directly by the use of DA agonists or antagonists. Yet another treatment strategy was to modulate synaptic DA, indirectly or trans-synaptically, by specifically targeting a functionally-linked but biochemically different neurotransmitter system.

A number of drugs have been suggested for use in weaning cocaine users from their dependency. Certain therapeutic agents were favored by the "dopamine depletion hypothesis." It is well established that cocaine blocks dopamine reuptake, acutely increasing synaptic dopamine concentrations. However, in the presence of cocaine, synaptic dopamine is metabolized as 3-methoxytyramine and excreted. The synaptic loss of dopamine places demands on the body for increased dopamine synthesis, as evidenced by the increase in tyrosine hydroxylase activity after cocaine administration. When the precursor supplies are exhausted, a dopamine deficiency develops. This hypothesis led to the testing of bromocriptine, a dopamine receptor agonist. Another approach was the administration of amantadine, a dopamine releaser. Yet another approach, also based on the dopamine depletion hypothesis, was to provide a precursor for dopamine, such as L-dopa.

Agonists are not preferred therapeutic agents. A given agonist may act on several receptors, or similar receptors on different cells, not just on the particular receptor or cell one desires to stimulate. As tolerance to a drug develops (through changes in the number of receptors and their affinity for the drug), tolerance to the agonist may likewise develop. A particular problem with the agonist bromocriptine, for example, is that it may itself create a drug dependency. Thus, treatment strategies used in the past did not relieve the patient's craving for cocaine. Moreover, by using certain agonists such as bromocriptine, a patient was likely to replace one craving for another.

Another drug that is frequently abused is nicotine. The alkaloid (-)-nicotine is present in cigarettes and other tobacco products that are smoked or chewed. It has been found that nicotine contributes to various diseases, including cancer, heart disease, respiratory disease and other conditions, for which tobacco use is a risk factor, particularly heart disease.

Vigorous campaigns against the use of tobacco or nicotine have taken place, and it is now common knowledge that the cessation of tobacco use brings with it numerous unpleasant withdrawal symptoms, which include irritability, anxiety, restlessness, lack of concentration, lightheadedness, insomnia, tremor, increased hunger and weight gain, and, of course, an intense craving for tobacco.

The addictive liability of nicotine has been linked to the rewarding/reinforcing actions and its effects on DA neurons in the reward pathways of the brain (Nisell et al., 1995; Pontieri, et al., 1996). For example, the acute systemic administration of nicotine, as well as numerous other drugs of abuse, produces an increase in extracellular DA levels in the nucleus accumbens (NACC), an important component of the reward system (Damsma et al., 1989; Di Chiara and Imperato, 1988; Imperato et al., 1986; Nisell et al., 1994a, 1995; Pontieri et al., 1996). Similarly, the infusion of nicotine into the ventral segmental area (VTA) of the rodent produces a significant increase in DA levels in the NACC (Nisell et al., 1994b).

A few pharmaceutical agents have been reported as useful to treat nicotine dependence, including nicotine substitution therapy such as nicotine gum, transdermal nicotine patches, nasal sprays, nicotine inhalers and bupropion, the first nonnicotinic treatment for smoking cessation (Henningfield, 1995; Hurt, et al., 1997).

Unfortunately, nicotine substitution therapy involves the administration of the nicotine which frequently leads to nicotine withdrawal and subsequent relapse to use of tobacco products. Thus, there is a need for a therapy having a desirable side effect profile, to relieve nicotine withdrawal symptoms, including the long term cravings for nicotine.

Other well known addictive substances are narcotic analgesics such as morphine, heroin and other opioids both natural and semisynthetic. Abuse of opioids induce tolerance and dependence. Withdrawal symptoms from the cessation of opioids use vary greatly in intensity depending on numerous factors including the dose of the opioid used, the degree to which the opioid effects on the CNS are continuously exerted, the duration of chronic use, and the rate at which the opioid is removed from the receptors. These withdrawal symptoms include craving, anxiety, dysphoria, yawning, perspiration, lacrimation, rhinorrhoea, restless and broken sleep, irritability, dilated pupils, aching of bones, back and muscles, piloerection, hot and cold flashes, nausea, vomiting, diarrhea, weight loss, fever, increased blood pressure, pulse and respiratory rate, twitching of muscles and kicking movements of the lower extremities.

Medical complications associated with injection of opioids include a variety of pathological changes in the CNS including degenerative changes in globus pallidus, necrosis of spinal gray matter, transverse myelitis, amblyopia, plexitis, peripheral neuropathy, Parkinsonian syndromes, intellectual impairment, personality changes, and pathological changes in muscles and peripheral nerves. Infections of skin and systemic organs are also quite common including staphylococcal pneumonitis, tuberculosis, endocarditis, septicemia, viral hepatitis, human immunodeficiency virus (HIV), malaria, tetanus and osteomyelitis. The life expectancy of opioid addicts is markedly reduced, due to overdose, drug-related infections, suicide and homicide.

Pharmaceutical agents used in treating opioid dependence include methadone, which is an opioid, and opioid antagonists, primarily naloxone and naltrexone. Clonidine has been shown to suppress some elements of opioid withdrawal but suffers from the side effects of hypotension and sedation, which can be quite extreme. Behavior-modifying psychological treatment and training are frequently adjunctive therapy used in association with pharmaceutical agents. There is a need for a therapy having a more desirable side effect profile, to relieve opioid addiction and withdrawal symptoms.

Ethanol is probably the most frequently used and abused depressant in most cultures and a major cause of morbidity and mortality. Repeated intake of large amounts of ethanol can affect nearly every organ system in the body, particularly the gastrointestinal tract, cardiovascular system, and the central and peripheral nervous systems. Gastrointestinal effects include gastritis, stomach ulcers, duodenal ulcers, liver cirrhosis, and pancreatitis. Further, there is an increased rate of cancer of the esophagus, stomach and other parts of the gastrointestinal tract. Cardiovascular effects include hypertension, cardiomyopathy and other myopathies, significantly elevated levels of triglycerides and low-density lipoprotein cholesterol. These cardiovascular effects contribute to a marked increase risk of heart disease. Peripheral neuropathy may be present as evidenced by muscular weakness, parathesias, and decreased peripheral sensation. Central nervous system effects include cognitive deficits, severe memory impairment degenerative changes in the cerebellum, and ethanol-induced persisting amnesiac disorder in which the ability to encode new memory is severely impaired. Generally, these effects are related to vitamin deficiencies, particularly the B vitamins.

Individuals with ethanol dependence or addiction exhibit symptoms and physical changes including dyspepsia, nausea, bloating, esophageal varices, hemorrhoids, tremor, unsteady gait, insomnia, erectile dysfunction, decreased testicular size, feminizing effects associated with reduced testosterone levels, spontaneous abortion, and fetal alcohol syndrome. Symptoms associated with ethanol cessation or withdrawal include nausea, vomiting, gastritis, hematemises, dry mouth, puffy blotchy complexion, and peripheral edema.

The generally accepted treatment of ethanol addiction and withdrawal is accomplished by administering a mild tranquilizer such a chlordiazepoxide. Typically, vitamins, particularly the B vitamins, are also administered. Optionally, magnesium sulfate and/or glucose are also administered. Nausea, vomiting and diarrhea are treated symptomatically at the discretion of the attending physician. Disulfiram may also be administered for help in maintaining abstinence. If ethanol is consumed while on disulfiram, acetaldehyde accumulates producing nausea and hypotension. There is a need for a therapy having a more desirable side effect profile, to relieve ethanol addiction and withdrawal symptoms.

Accordingly, there is still a need in the treatment of addiction to drugs of abuse to provide new methods which can relieve a patient's craving by changing the pharmacological actions of drugs of abuse in the central nervous system.

SUMMARY OF THE PRESENT INVENTION

The present invention, which addresses the needs of the prior art, provides methods for treating substance addiction and changing addiction-related behavior of a mammal, for example a primate, suffering from substance addiction by administering to the mammal an effective amount of a pharmaceutical composition including gamma vinylGABA (GVG). The amount of GVG varies from about 15 mg/kg to about 2 gm/kg, preferably from about 100 mg/kg to about 600 mg/kg, and most preferably from about 150 mg/kg to about 300 mg/kg.

In a preferred embodiment, the present invention provides a method of eliminating the effects of nicotine addiction by treating a mammal with an effective amount of a composition including GVG. When treating the effects of nicotine addiction the amount of GVG present in the pharmaceutical composition is from about 15 mg/kg to about 2 g/kg. Preferably, 75 mg/kg to about 150 mg/kg, and most preferably from about 18 mg/kg to about 20 mg/kg.

In yet another embodiment, the present invention provides a method for changing addiction-related behavior of a mammal suffering from addiction to drugs of abuse which comprises administering to the mammal an effective amount of gamma vinylGABA (GVG) or a pharmaceutically acceptable salt thereof, wherein the effective amount attenuates the rewarding/incentive effects of drugs of abuse selected from the group consisting of psychostimulants, narcotic analgesics, alcohols, nicotine and combinations thereof in the absence of altering rewarding/incentive effects of food in said mammal.

The amount of GVG varies from about 15 mg/kg to about 2 gm/kg, preferably from about 15 mg/kg to about 600 mg/kg, and most preferably from about 150 mg to about 600 mg/kg.

As a result of the present invention, methods of reducing substance addiction and changing addiction-related behavior are provided which are based on a pharmaceutical composition which is not itself addictive, yet is highly effective in ameliorating the addiction and the addictive behavior of addicted patients. The pharmaceutical composition useful for the method of the present invention inhibits or eliminates craving experienced by drug addicts for use of the drug of abuse. Moreover, the elimination of behavior associated with drugs of abuse occurs in the absence of an aversive or appetitive response to GVG. Moreover, behavior characteristics associated with dependency on drugs of abuse are reduced or eliminated in the absence of an alteration in the locomotor function of the primate.

In yet another embodiment, the invention includes a method for changing addiction-related behavior of a mammal suffering from addiction to drugs of abuse which comprises administering to the mammal an effective amount of gamma vinylGABA (GVG) or a pharmaceutically acceptable salt thereof, or an enantiomer or a racemic mixture thereof, wherein the effective amount is sufficient to diminish, inhibit or eliminate behavior associated with craving or use of drugs of abuse.

In another exemplary embodiment of the present invention, the method includes changing addiction-related behavior of a mammal suffering from addiction to drugs of abuse which comprises administering to the mammal an effective amount of a composition that increases central nervous system GABA levels wherein the effective amount is sufficient to diminish, inhibit or eliminate behavior associated with craving or use of drugs of abuse.

Other improvements which the present invention provides over the prior art will be identified as a result of the following description which sets forth the preferred embodiments of the present invention. The description is not in any way intended to limit the scope of the present invention, but rather only to provide a working example of the present preferred embodiments. The scope of the present invention will be pointed out in the appended claims.

BRIEF DESCRIPTIONS OF THE DRAWINGS

FIG. 2 is a photograph of transaxial parametric DV ratio images of the non-human primate brain at the level of the corpus striatum.

FIG. 5A and 5B are graphs illustrating the effects of nicotine and GVG on extracellular dopamine levels in the nucleus accumbens of freely moving rats.

DETAILED DESCRIPTION OF THE INVENTION

Figure 1:
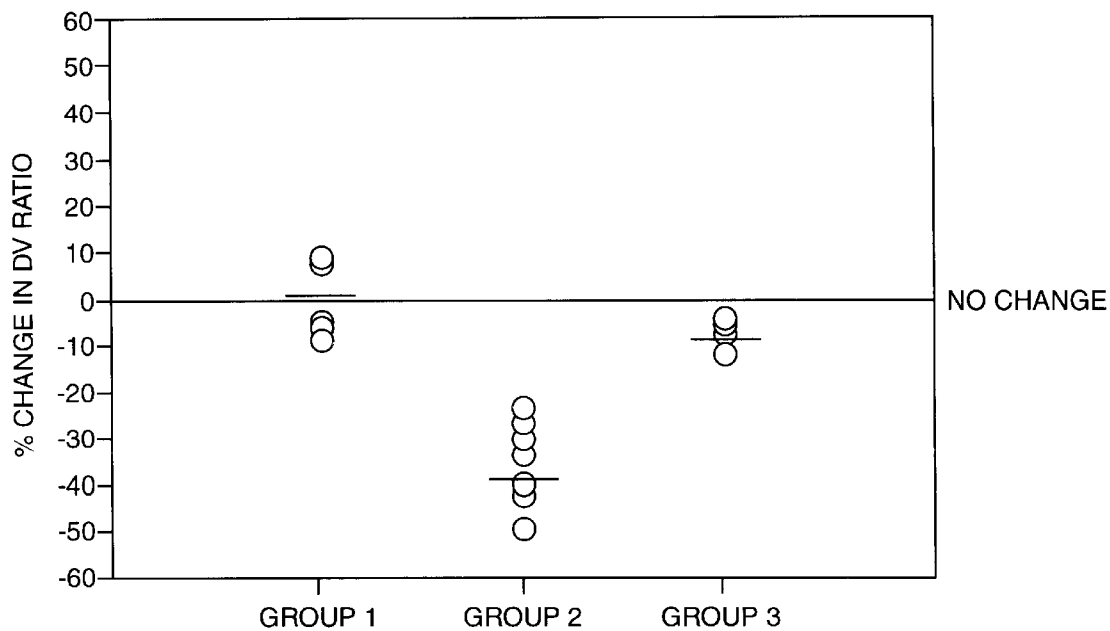
FIG. 1 is a graph illustrating percent change in distribution volume (DV) for three groups of animals treated with cocaine.

The present invention provides a highly efficient method for treating substance addiction and for changing addiction-related behavior of mammals, for example primates, suffering from substance addiction.

As used herein, addiction-related behavior means behavior resulting from compulsive substance use and is characterized by apparent total dependency on the substance. Symptomatic of the behavior is (i) overwhelming involvement with the use of the drug, (ii) the securing of its supply, and (iii) a high probability of relapse after withdrawal.

For example, a cocaine user experiences three stages of drug effects. The first, acute intoxication ("binge"), is euphoric, marked by decreased anxiety, enhanced self-confidence and sexual appetite, and may be marred by sexual indiscretions, irresponsible spending, and accidents attributable to reckless behavior. The second stage, the ("crash"), replaces euphoria by anxiety, fatigue, irritability and depression. Some users have committed suicide during this period. Finally, the third stage, "anhedonia," is a time of limited ability to derive pleasure from normal activities and of craving for the euphoric effects of cocaine which leads to use of this drug. See Gawin and Kleber, Medical Management of Cocaine Withdrawal, 6–8 (APT Foundation). As related to cocaine users, addiction-related behavior includes behavior associated with all three stages of drug effects.

Drugs of abuse include but are not limited to psychostimulants, narcotic analgesics, alcohols and addictive alkaloids such as nicotine or combinations thereof. Some examples of psychostimulants include but are not limited to amphetamine, dextroamphetamine, methamphetamine, phenmetrazine, diethylpropion, methylphenidate, cocaine and pharmaceutically acceptable salts thereof.

Specific examples of narcotic analgesics include alfentanyl, alphaprodine, anileridine, bezitramide, codeine, dihydrocodeine, diphenoxylate, ethylmorphine, fentanyl, heroin, hydrocodone, hydromorphone, isomethadone, levomethorphan, levorphanol, metazocine, methadone, metopon, morphine, opium extracts, opium fluid extracts, powdered opium, granulated opium, raw opium, tincture of opium, oxycodone, oxymorphone, pethidine, phenazocine, piminodine, racemethorphan, racemorphan, thebaine and pharmaceutically acceptable salts thereof.

Drugs of abuse also include CNS depressants such as barbiturates, chlordiazepoxide, and alcohols such as ethanol, methanol and isopropyl alcohol.

Compulsive drug use includes three independent components: tolerance, psychological dependence and physical dependence. Tolerance produces a need to increase the dose of the drug after several administration in order to achieve the same magnitude of effect. Physical dependence is an adaptive state produced by repeated drug administration and which manifests itself by intense physical disturbance when drug administration is halted. Psychological dependence is a condition characterized by an intense drive, craving or use for a drug whose effects the user feels are necessary for a sense of well being. See Feldman, R. S. and Quenzer, L. F. "Fundamentals of Neuropsychopharmocology" 418–422 (Sinaur Associates, Inc.) 1984 incorporated herein by reference as if set forth in full. Based on the foregoing definitions, as used herein "dependency characteristics" include all characteristics associated with compulsive drug use, characteristics that can be affected by biochemical composition of the host, physical and psychological properties of the host.

As explained above, the compulsive use of drugs of abuse gives rise to a euphoric stage followed by a stage of craving for the euphoric effects of that drug which leads to use of the drug. As used herein the rewarding/incentive effects of drugs of abuse refers to any stimulus (in this case, a drug) that produces anhedonia or increases the probability of a learned response. This is synonymous with reinforcement. With respect to experimental animals, a stimulus is deemed to be rewarding by using paradigms that are believed to measure reward. This can be accomplished by measuring whether stimuli produce an approach response, also known as an appetitive response or a withdrawal response, as when the animal avoids the stimuli, also known as an aversive response. Conditioned place preference (CPP) is a paradigm which measures approach (appetitive) or withdrawal (aversive) responses. One can infer that rewarding stimuli produce approach behavior. In fact, one definition of reward is any stimulus that elicits approach behavior. Furthermore, the consequences of reward would be to enhance the incentive properties of stimuli associated with the reward.

Reward can also be measured by determining whether the delivery of a reward is contingent upon a particular response, thereby increasing the probability that the response will reappear in a similar situation, i.e. reinforcement paradigm. For example, a rat pressing a bar a certain number of times for an injection of cocaine is an example of reinforcement. Yet another way to measure reward is by determining if a stimulus (e.g. a drug), through multiple pairings with neutral environmental stimuli, can cause the previously neutral environmental stimuli to elicit behavioral effects initially only associated with the drug—this conditioned reinforcement. CPP is considered to be a form of conditioned reinforcement.

The incentive motivational value of a drug (or other stimuli) can be assessed using conditioned place preference (CPP). With respect to cocaine, nicotine, heroin, morphine methamphetamine, ethanol or other drugs of abuse, animals are tested in a drug-free state, to determine whether they prefer an environment in which they previously received the abused drug as compared to an environment in which they previously received saline. In the CPP paradigm, animals are given a drug in one distinct environment and are given the appropriate vehicle in an alternative environment. The CPP paradigm is widely used to evaluate the incentive motivational effects of drugs in laboratory animals (Van Der Kooy, 1995). Following conditioning or pairing with the drug if the animal, in a drug-free state, consistently chooses the environment previously associated with the drug of abuse, the inference is drawn that the appetitive value of the drug of abuse was encoded in the brain and is accessible in the drug-free state. CPP is reflected in an increased duration spent in the presence of the drug-associated stimuli relative to vehicle-injected control animals.

It has been postulated that since craving at the human level is often elicited by sensory stimuli previously associated with drug-taking, conditioning paradigms like CPP may be used to model craving in laboratory animals.

The addictive liability of drugs of abuse, such as for example, cocaine, nicotine, methamphetamine, morphine, heroin, ethanol or other drugs of abuse has been linked to their pharmacological actions on mesotelencephalic dopamine (DA) reinforcement/reward pathways in the central nervous system (CNS). Dopaminergic transmission within these pathways is modulated by gamma-amino butyric acid (GABA).

For example cocaine, nicotine, methamphetamine, morphine, heroin and ethanol inhibit the presynaptic reuptake of monoamines. Dopaminergic neurons of the mesocorticolimbic DA system, whose cell bodies lie within the ventral tegmental area (VTA) and project primarily to the nucleus accumbens (NACC), appear to be involved in cocaine, nicotine, methamphetamine, morphine, heroin or ethanol reinforcement. Electrical stimulation of reward centers within the VTA increases extracellular DA levels in the NACC, while 6-hydroxy dopamine lesions of the NACC abolish cocaine, nicotine, methamphetamine, morphine, heroin or ethanol self-administration. In vivo microdialysis studies confirm cocaine, nicotine, methamphetamine, morphine, heroin and ethanol's ability to increase extracellular DA in the NACC.

γ-Amino butyric acid (GABA)ergic neurons in the NACC and ventral pallidum project onto DA neurons in the VTA. Pharmacologic and electrophysiologic studies indicate these projections are inhibitory. Inhibition of VTA-DA neurons is likely the result of $GABA_B$ receptor stimulation. In addition, microinjection of baclofen into the VTA, acting via these receptor subtypes, can decrease DA concentrations in the NACC. Taken together, it is evident that pharmacologic manipulation of GABA may effect DA levels in the NACC through modulation of VTA-DA neurons.

Gamma vinyl GABA (GVG) is a selective and irreversible inhibitor of GABA-transaminase (GABA-T) known to potentiate GABAergic inhibition. It is also known that GVG alters cocaine's biochemical effects by causing a dose-dependent and prolonged elevation of extracellular endogenous brain GABA levels.

GVG is $C_6H_{11}NO_2$ or 4-amino-5-hexanoic acid available as Vigabatrin® from Hoechst Marion Roussel and can be obtained from Marion Merell Dow of Cincinnati, Ohio. GVG does not bind to any receptor or reuptake complex, but increases endogenous intracellular GABA levels by selectively and irreversibly inhibiting GABA-transaminase (GABA-T), the enzyme that normally catabolizes GABA.

As used herein GVG includes the racemic compound or mixture which contains equal amounts of S(+)-gamma-vinyl GABA, and R(−)-gamma vinyl GABA. This racemic compound of GVG is available as Vigabatrin® from Hoechst Marion Roussel and can be obtained from Marion Merell Dow of Cincinnati, Ohio.

GVG contains asymmetric carbon atoms and thus is capable of existing as enantiomers. The present invention embraces any enantiomeric form of GVG including the racemates or racemic mixture of GVG. In some cases there may be advantages, i.e. greater efficacy, to using a particular enantiomer when compared to the other enantiomer or the racemate or racemic mixture in the methods of the instant invention and such advantages can be readily determined by those skilled in the art.

For example, the enantiomer S(+)-gamma-vinyl GABA is more effective at increasing endogenous intracellular GABA levels than the enantiomer R(−)-gamma-vinyl GABA.

Different enantiomers may be synthesized from chiral starting materials, or the racemates may be resolved by conventional procedures which are well known in the art of chemistry such as chiral chromatography, fractional crystallization of diastereomeric salts, and the like.

In living mammals (in vivo), GVG or pharmaceutically acceptable salts thereof, can be administered systemically by the parenteral and enteral routes which also includes controlled release delivery systems. For example, GVG can easily be administered intravenously, or intraperitoneal (i.p.) which is a preferred route of delivery. Intravenous or intraperitoneal administration can be accomplished by mixing GVG in a suitable pharmaceutical carrier (vehicle) or excipient as understood by practitioners in the art.

Oral or enteral use is also contemplated, and formulations such as tablets, capsules, pills, troches, elixirs, suspensions, syrups, wafers, chewing gum and the like can be employed to provide GVG or pharmaceutically acceptable salts thereof.

As used herein, pharmaceutically acceptable salts include those salt-forming acids and bases which do not substantially increase the toxicity of the compound. Some examples of suitable salts include salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g. p-toluenesulfonic acids, and the like.

An effective amount as used herein is that amount effective to achieve the specified result of changing addiction-related behavior of the mammal. It is an amount which will diminish or relieve one or more symptoms or conditions resulting from cessation or withdrawal of the psychostimulant, narcotic analgesic, alcohol, nicotine or combinations thereof Preferably, GVG is administered in an amount which has little or no adverse effects. The amount administered can be from about 15 mg/kg to about 2 g/kg or from about 15 mg/kg to about 600 mg/kg.

For cocaine addiction, GVG is administered in an amount of from about 15 mg/kg to about 2 g/kg, preferably from about 100 mg/kg to about 300 mg/kg or from about 15 mg/kg to about 600 mg/kg and most preferably from about 150 mg/kg to about 300 mg/kg or from about 75 mg/kg to about 150 mg/kg.

For nicotine addiction, GVG is administered in an amount of from about 15 mg/kg to about 2 g/kg or from about 15 mg/kg to about 600 mg/kg, preferably from about 100 mg/kg to about 300 mg/kg or from about 150 mg/kg to about 300 mg/kg and most preferably from about 18 mg/kg to about 20 mg/kg or from about 75 mg/kg to about 150 mg/kg.

For methamphetamine addiction, GVG is administered in an amount of from about 15 mg/kg to about 2 g/kg, preferably from about 100 mg/kg to about 300 mg/kg or from about 15 mg/kg to about 600 mg/kg and most preferably from about 150 mg/kg to about 300 mg/kg or from about 75 mg/kg to about 150 mg/kg to a mammal.

Mammals include, for example, humans, baboons and other primates, as well as pet animals such as dogs and cats, laboratory animals such as rats and mice, and farm animals such as horses, sheep, and cows.

Gamma vinyl GABA (GVG) is a selective and irreversible inhibitor of GABA-transaminase (GABA-T) known to potentiate GABAergic inhibition. It is also known that GVG alters cocaine's biochemical effects by causing a dose-dependent and prolonged elevation of extracellular endogenous brain GABA levels.

Based on the knowledge that cocaine, as well as other drugs of abuse, increases extracellular NACC DA and the fact that GABA inhibits DA in the same nuclei, we have shown that GVG can attenuate cocaine, nicotine, methamphetamine, and ethanol-induced changes in extracellular DA. In one example, in vivo microdialysis techniques were used in freely moving animals to show, the effects of acute (single injection) and chronic (11 days) GVG administration on cocaine-induced increases in extracellular DA concentration in the NACC. See specifically Morgan, A.E., et al. "Effects of Pharmacologic Increases in Brain ABA Levels on Cocaine—Induced Changes in Extracellular Dopamine," Synapse 28:60–65 (1998) the contents of which are incorporated herein as if set forth in full.

It has unexpectedly been found that intake of GVG alters behavior, and especially addiction-related behavior associated with the biochemical changes resulting from intake of drugs of abuse. For example, GVG significantly attenuated cocaine-induced increases in neostriatal synaptic DA in the primate (baboon) brain as assessed by positron emission tomography (PET) and abolished both the expression and acquisition of cocaine-induced conditioned place preference or CPP. It had no effect, however, on CPP for a food reward or on the delivery of cocaine to the brain locomotor activity. These findings suggest the possible therapeutic utility in cocaine addiction of a pharmacologic strategy targeted at the GABAergic neurotransmitter system, a system distinct from but functionally linked to the DA mesotelencephalic reward/reinforcement system. However, rather than targeting the GABA receptor complex with a direct GABA agonist, this novel approach with GVG takes advantage of the prolonged effects of an irreversible enzyme inhibitor that raises endogenous GABA levels without the addictive liability associated with GABA agonists acting directly at the receptor itself.

In addition, the method of the present invention can be used to treat mammals addicted to a combination of drugs of abuse. For example, the mammal may be addicted to ethanol and cocaine, in which case the present invention is particularly suited for changing addiction-related behavior of the mammal by administering an effective amount of GVG.

Although GVG is used in the present examples, it will be understood by those skilled in the arts that other compositions can be used which are known to potentiate the GABAergic system or increase extracellular endogenous GABA levels in the CNS.

Such compositions include drugs which enhance the production or release of GABA in the CNS. These drugs include, but are not limited to, gabapentin, valproic acid, progabide, gamma-hydroxybutyric acid, fengabine, cetylGABA, topiramate, tiagabine, acamprosate (homo calcium acetyltaurine) or a pharmaceutically acceptable salt thereof, or an enantiomer or a racemic mixture thereof.

The present invention embraces any enantiomeric form of gabapentin, valproic acid, progabide, gamma-hydroxybutyric acid, fengabine, cetylGABA, topiramate, tiagabine, or acamprosate, including the racemates or racemic mixtures thereof.

As previously stated, in some cases there may be advantages, i.e. greater efficacy, to using a particular enantiomer when compared to the other enantiomer or the racemate or racemic mixture in the methods of the instant invention and such advantages can be readily determined by those skilled in the art.

The present invention embraces compositions which include prodrugs of GABA or drugs which contain GABA as a moiety in its chemical structure. These prodrugs become pharmacologically active when metabolically, enzymatically or non-enzymatically biotransformed or cleaved into GABA in the CNS. An example of a prodrug of GABA is progabide which, upon crossing the blood brain barrier, increases endogenous CNS GABA levels.

As previously stated, Gamma vinyl GABA (GVG) is a selective and irreversible inhibitor of GABA-transaminase (GABA-T) known to potentiate GABAergic inhibition. Other compositions which inhibit GABA re-uptake in the CNS are also encompassed by the present invention. An example of a GABA re-uptake inhibitor is tiagabine.

The method of the present invention is useful in potentiating the GABAergic system or increasing extracellular endogenous GABA levels in the CNS. As used herein, enhancing or increasing endogenous CNS GABA levels is defined as increasing or up-regulating GABA levels substantially over normal levels in vivo, within a mammal. Preferably, endogenous CNS GABA levels are enhanced at least by from about 10% to about 600% over normal levels.

As previously stated, an effective amount as used herein is that amount effective to achieve the specified result of changing addiction-related behavior of the mammal. It is an amount which will diminish or relieve one or more symptoms or conditions resulting from cessation or withdrawal of the psychostimulant, narcotic analgesic, alcohol, nicotine or combinations thereof.

For example, an effective amount of gabapentin administered to the mammal is an amount from about 500 mg to about 2 g/day. Gabapentin is available as Neurontin® from Parke-Davis in the United States.

An effective amount of valproic acid administered to the mammal is preferably, an amount from about 5 mg/kg to about 100 mg/kg /day. Valproic acid is available as Depakene® from Abbott in the United States.

Preferably, an effective amount of topiramate administered to the mammal is an amount from about 50 mg to about 1 g/day. Topiramate is available as Topamax® from McNeil in the United States. An effective amount of progabide administered to the mammal is, preferably, an amount from about 250 mg to about 2 g/day. Progabide is available as Gabrene® from Synthelabo, France. The chemical formula of progabide is $C_{17}H_{16}N_2O_2$.

An effective amount of fengabine administered to the mammal is, preferably, an amount from about 250 mg to about 4 g/day. Fengabine is available as SL 79229 from Synthelabo, France. The chemical formula of fengabine is $C_{17}H_{17}C_{12}NO$.

Preferably, an effective amount of gamma-hydroxybutyric acid administered to the mammal is an amount from about 5 mg/kg to about 100 mg/kg/day. Gamma-hydroxybutyric acid is available from Sigma Chemical. The chemical formula of gamma-hydroxybutyric acid is $C_4H_7O_3Na$.

Details of the invention have been set forth herein in the form of examples which are described below. The full scope of the invention will be pointed out in the appended claims.

EXAMPLES

Examples have been set forth below for the purpose of illustration and to describe the best mode of the present invention. The scope of the invention is not to be in any way limited by the examples set forth herein.

Materials and Methods
1. Primate PET Studies

Twenty adult female baboons (Papio anubis, 13–18 kg) were used for all studies and carbon-11 labeled raclopride, previously shown to be sensitive to changes in synaptic DA was synthesized as previously described (Volkow, et al., 1994). Arterial blood samples were obtained throughout the study and selected plasma samples were analyzed for the presence of unchanged radio tracer carbon-11. Animals were not removed from the gantry between isotope injections. Regions of interest (ROI's) were drawn directly on the PET images. Briefly, the corpus striatum was outlined, bilaterally, on every transaxial slice upon which it appeared. The cerebellar ROI was drawn across the midline at the level of the cerebellar vermis. ROI's from the first study were then copied directly onto the corresponding slice from the second. By examining placement of the ROI's on the second scan changes could be made, if necessary, in ROI position only. This multi planar method of analysis reduced differences that may arise due to movement of the animal within the gantry during the scanning interval.

A graphical method for determining the distribution volume (DV) was developed previously for the kinetic analysis of the [$^{11}$C]-raclopride data. The DV ratio was the most reproducible measure of raclopride uptake. The ratio is the DV from a receptor-rich region (corpus striatum) to the DV of a non-receptor region (cerebellum). The free receptor concentration was directly proportional to the DV ratio of 1. Animal preparation was conducted as detailed previously (Dewey, et al., 1992).

The statistical analysis was designed to test the hypothesis that (1) the cocaine challenge differed from the test/retest variability of the radio tracer carbon-11 (performed in the same animals under identical experimental conditions) and (2) the challenge conditions differed from each other. The fact that significant results were obtained for the striatum and striatum to cerebellum ratio, but not for the cerebellum, indicated that the effects of the intervention were limited to the specific, but not the non-specific binding component. GVG did not alter the regional distribution nor the rate of metabolism of the radio tracer.

2. Cocaine-Induced Conditioned Place Preference in Rodents

In all rodent studies, male Sprague-Dawley rats were used (200–225 g, Taconic farms, Germantown, N.Y.). Animals were allowed to acclimate to the animal housing facility for at least 5 days prior to beginning the experiments. We used conditioned place preference (CPP) chambers as previously described (Lepore et al., 1995), except instead of one chamber being entirely white and the other black, one chamber was entirely light blue with a stainless steel floor and the second chamber was light blue with horizontal black stripes (2.5 cm wide) spaced 3.8 cm apart with a smooth plexiglass floor. In all CPP studies with GVG, the saline volume was (1 ml/kg), and the cocaine doses were 20 mg/kg. The saline, cocaine and GVG were all injected intraperitonealy (i.p.). The conditioning procedure for the acquisition phase consisted of 12 sessions carried out consecutively over 12 days.

The CPP pairings were: 1) saline/saline 2) saline/cocaine 3) GVG/saline 4) saline/cocaine and GVG. The animals in each group were randomly assigned to a 2×2 factorial design with one factor being the pairing chamber and the other factor being the order of conditioning. The animals that received either saline or cocaine were injected and confined to the appropriate compartment for 30 minutes. The GVG injections were given 3 hours before saline or cocaine injection and subsequent placement of the animals in the appropriate chamber. This was done as it has been shown that GABA levels reach maximal values 3 to 4 hours following GVG administration.

On the test day (day 12), neither drugs nor saline were administered and the animal was allowed to move freely between both chambers for fifteen minutes. The amount of time spent in each chamber was recorded using an automated infrared beam electronically coupled to a timer. For the expression phase of CPP to cocaine, the animals were habituated and conditioned to cocaine as described in the acquisition studies, but no animals in the expression studies were given GVG on conditioning days. On the test day (day 12), the animals being tested in the expression phase, unlike the animals in the acquisition phase, received either saline or GVG 2.5 hours before they were placed in the apparatus and allowed free access to both chambers for 15 minutes.

3. Food-Induced Conditioned Place Preference in Rodents

In order to test food-induced CPP in rodents, four groups of rats were allowed access to food ad libitum during the entire 12 session of CPP procedure. The 12 session CPP procedure was exactly the same as the procedure used in the cocaine induced CPP studies except the appetitive substance was food rather than cocaine. Group one was given saline, group two was given intraperitoneally 150 mg/kg of GVG, group 3 was given saline and group 4 was given intraperitoneally 300 mg/kg of GVG prior to food exposure and CPP pairing to a side of the CPP box. The animals in all four groups were habituated to Froot Loops, a fruit-flavored breakfast cereal that is very appealing to laboratory rats, in the appropriate chamber in the test room during four habituating sessions. Twenty-four hours after the last CPP pairing, the animals were placed in the chamber and neither drug nor saline (nor food) was administered (nor available) and animals were allowed to move freely within the CPP apparatus for 15 minutes. The amount of time spent in the paired and unpaired chambers was recorded using an automated device.

4. Locomotor Activity Measured in Rodents

Animals were prehandled for 5 minutes each day for one week prior to the experiment to reduce handling stress. On the day of the study, GVG (150 mg/kg or 300 mg/kg) or saline (1 ml/kg or 0.5 ml/kg) was administered intraperitoneally 2.5 hours prior to the experiment. The animals were transported to the testing area one hour before each experiment. 2.5 hours after GVG or saline administration, animals were placed in the behavior cages and the locomotor activity was recorded in 10 minute intervals for 90 minutes onto a PC-AT computer using the hardware for the Photobeam Activity System. The locomotor cages themselves are 41.3× 41.3×30.5 cm clear acrylic cages. The electronic system (Photobeam Activity system, San Diego Instruments, San Diego, Calif.) used to monitor locomotor activity consists of 16 infrared beams projecting across the cages from left to right and 16 beams from front to back. All the infrared beams are approximately 0.39 cm from the floor.

5. Catalepsy Studies in Rodents

The degree of catalepsy following the administration intraperitoneally of 150 mg/kg GVG, 300 mg/kg intraperitoneally GVG or saline (1 ml/kg, i.p. 0.9% saline) was determined by using the Bar test. Briefly, male Sprague-Dawley rats were handled and transported to the test room three days prior to the experiments to allow for acclimation. On the test day, the animals (n=10 per treatment group) received either saline or GVG, and the degree of catalepsy was measured 60, 120 and 240 minutes following injection. The experimenter was blind to the treatment received by each animal. The bar was composed of wood and had a diameter of 1.2 cm and height from floor to the top of the bar was 10 cm. For each determination, the forepaws of the animals were gently placed over the bar and the time it took the animal to move both forepaws to the floor was measured.

6. [$^{11}$C]-Cocaine Studies in Rodents and Primates

Animals (n=10) were placed into two groups. In group 1, saline (1 ml/kg) was administered via intraperitoneal (i.p.) injection 3 hours prior to i.p. [$^{11}$C]-cocaine administration. In group 2, GVG (300 mg/kg) was administered via i.p. injection 3 hours prior to i.p. [$^{11}$C]-cocaine administration. Animals were sacrificed 10 minutes following [$^{11}$C]-cocaine injection. Brains were removed and counted for radioactivity. In two additional primate PET studies, GVG was administered (300 mg/kg) immediately following a baseline scan with labeled cocaine. Approximately 3 hours later, labeled cocaine was again administered and animals were scanned for 60 minutes.

7. Microdialysis studies in Rodents

All animals were used under an IACUC-approved protocol and with strict adherence to the NIH guidelines. Adult male Sprague-Dawley rats (200–300 g, Taconic Farms), housed in the animals care facility under 12:12 light/dark conditions, were placed into 6 groups (n=5–9), anesthetized and siliconized guide cannulae were stereotactically implanted into the right NACC (2.0 mm anterior and 1.0 mm lateral to bregms, and 7.0 mm ventral to the cortical surface) at least 4 days prior to study. Microdialysis probes (2.0 mm, Bioanalytical Systems, BAS, West Lafayette, Ind.) were positioned within the guide cannulae and artificial cerebrospinal fluid (ACSF, 155.0 mM $NA^-$ 1.1 mM $Ca^{2-}$, 2.9 mM $K^-$, 132.76 mM $Cl^-$, and 0.83 mM $Mg^{2-}$) was administered through the probe using a CMA/100 microinfusion pump (BAS) at a flow rate of 2.0 $\mu$l/min. Animals were placed in bowls, and probes were inserted and flushed with ACSF overnight. On the day of the study, a minimum of three samples were injected to determine baseline stability. Samples were collected for 20 min. and injected on-line (CMA/160, BAS). The average Dopamine concentration of these three stable samples was defined as control (100%), and all subsequent treatment values were transformed to a percentage of that control. Upon establishing a stable baseline, the nicotine was administered by intraperitoneal (i.p.) injection. The high performance liquid chromatography (HPLC) system consists of a BAS reverse-phase column (3.0$\mu$C-18), a BAS LC-4C electrochemical transducer with a dual/glassy carbon electrode set at 650 mV, a computer that analyzes data on-line using a commercial software package (Chromograph Bioanalytical Systems), and a dual pen chart recorder. The mobile phase (flow rate 1.0 ml/min) consisted of 7.0% methanol, 50 mM sodium phosphate monobasic, 1.0 mM sodium octyl sulfate, and 0.1 mm EDNA, pH 4.0. DA eluted at 7.5 min. Upon completion of the study, animals were decapitated and frozen sections were obtained for probe placement verification.

In parallel to the quantitative estimates of dopamine concentration, the locomotor response of these animals to stimulant administration was simultaneously quantified using an infrared motion sensor. This infrared optical proximity detector monitored movement of the gimbaled arm, an integral component of the freely moving system. The digital output of the detector was interfaced with an IBM personal computer and programmed to count both positive and negative arm deflections. These data were collected and totaled using the same temporal sampling protocol used for the dialysis samples. Locomotor activity was then expressed as the number of deflections per sample interval.

Example 1

Non-Human Primate (Baboon) Studies

In this example twenty non-human primates received two [$^{11}$C]-raclopride injections in accordance with the procedure described in Section 1 of Materials and Methods. The first served as a baseline and the second followed cocaine or placebo. Test/retest primates (n=7) shown as Group 1 of Table 1 below received placebo (0.9% saline, 1 ml/kg) prior to the second radio tracer injection in order to determine the test/retest variability of this imaging method.

TABLE I

Groups and experimental conditions

| Group | Pharmacologic condition |
|---|---|
| 1 | Control (test/retest) |
| 2 | Cocaine treated |
| 3 | GVG/Cocaine treated |

All remaining primates (n=13) received a systemic injection of cocaine hydrochloride (0.5, 1.0 or 2.0 mg/kg) either 5 or 30 minutes prior to the second [$^{11}$C]-raclopride injection. Of these 13 animals, five received GVG (300 mg/kg, iv) 3 hours prior to cocaine administration.

Different cocaine doses and cocaine pretreatment time intervals produced no significant changes in the effects of cocaine on the distribution volume (DV), in line with expectations. Thus, the average % change in the DV ratio for animals treated with cocaine alone (n=8) versus GVG/cocaine (n=5) as Groups 2 and 3 of FIG. 1 respectively.

As a competitive antagonist, [$^{11}$C]-raclopride's binding is dependent upon the concentration of DA in the synaptic cleft. That is, as synaptic DA concentrations decrease, [$^{11}$C]-raclopride binding increases. Conversely, as synaptic DA concentrations increase, [$^{11}$C]-raclopride binding decreases. As seen in FIG. 1, the test/retest variability of this imaging method was less than 7% for group 1. The variability of these PET measurements is consistent with previous values obtained with [$^{11}$C]-raclopride in primates. In Group 2, cocaine produced a greater than 30% reduction in the mean DV ratio (p<0.0002, Student's two-tailed t-test, FIG. 1). These data are consistent with simultaneous PET and microdialysis studies in which an amphetamine challenge increased extracellular DA and decreased [$^{11}$C]-raclopride binding in the primate brain. In addition, these findings are similar to a recent report which examined the effects of a cocaine challenge on labeled raclopride binding in the human. Finally, these data are consistent with our own microdialysis studies (Morgan and Dewey, 1998) as well as our primate and human PET studies with amphetamine, GBR 12909, tetrabenazine, methylphenidate, and [$^{11}$C]-raclopride (Dewey et al., 1993; Volkow, et al., 1994). GVG pretreatment, however, significantly blocked the cocaine-induced decrease as shown in Group 2 of FIG. 1 in the DV ratio (group 2, p<0.002, Student's two-tailed t-test). These differences are readily apparent in the parametric DV ratio images as shown in FIG. 2. Values for groups 1 and 3 were not statistically different (p>0.1, Student's two-tailed t-test).

Example 2

Cocaine-Induced Conditioned Place Preference Studies in Rodents

In this example the procedure outlined in Section 2 of Materials and Methods was followed. Cocaine produced a dose-dependent CPP response, with the most reliable and robust response occurring at 20 mg/kg as shown in Table 2 below.

TABLE II

Conditioned place preference to cocaine

| | Time spent in chambers (mins) | |
|---|---|---|
| Cocaine (mg/kg) | Paired | Unpaired[1] |
| 0 | 7.4 ± 0.3 | 7.6 ± 0.3 |
| 5.0 | 8.2 ± 0.4 | 6.8 ± 0.5 |
| 10.0 | 9.6 ± 0.5[2] | 5.4 ± 0.3 |
| 20.0 | 11.8 ± 0.4[3] | 3.2 ± 0.4[4] |

[1]Monitored animals were injected only with saline
[2]Significantly greater than the 0 and 5 mg/kg doses of cocaine, p < 0.05, analysis of variance (ANOVA) and Student-Newman-Keuls test.
[3]Significantly greater than the 0.5 and 10 mg/kg doses of cocaine, p < 0.05, ANOVA and Student-Newman-Keuls test.
[4]Significantly less than 0.5 and 10 mg/kg doses of cocaine, p < 0.01, ANOVA and Student-Newman-Keuls test.

We therefore chose a 20 mg/kg cocaine dose with which to examine the effect of GVG administration on the acquisition and expression phases of cocaine-induced CPP. The results clearly indicated that 112, 150 and 300 mg/kg, but not 75 mg/kg, of GVG blocked the acquisition and expression of cocaine-induced CPP. See specifically Tables 3–10 below.

TABLE III

Effect of GVG and saline on the acquisition of cocaine induced conditioned place preference

| | Time spent in chambers (min) | |
|---|---|---|
| Treatment pairings[1] | Paired | Unpaired[2] |
| Saline/Saline | 7.3 ± 0.5 | 7.7 ± 0.6 |
| Saline/Cocaine | 11.1 ± 0.3[4] | 3.9 ± 0.4 |
| 75 mg/kg GVG[3]/Saline | 7.3 ± 0.5 | 7.7 ± 0.6 |
| 75 mg/kg GVG[3]/Cocaine | 9.1 ± 1.1 | 5.9 ± 1.2 |

[1]Each value represents the mean number of minutes spent in each chamber ± S.E.M. (n - 8–10).
[2]Monitored animals were injected only with saline.
[3]Animals received GVG or Saline 2.5 hours prior to receiving saline or cocaine (20 mg/kg).
[4]Significantly greater than all treatment groups, p < 0.05, ANOVA and Newman-Keuls Test.
[5]Significantly less than all treatment groups, p < 0.01, ANOVA and Newman-Keuls test.

TABLE IV

| | Time spent in chambers (mins) | |
|---|---|---|
| Treatment pairings[1] | Paired | Unpaired[2] |
| Saline/Saline | 7.2 ± 0.5 | 7.8 ± 0.4 |
| Saline/Cocaine | 11.8 ± 0.5[4] | 3.2 ± 0.5 |
| 112 mg/kg GVG[3]/Saline | 7.6 ± 0.6 | 7.4 ± 0.6 |
| 112 mg/kg GVG[3]/Cocaine | 8.2 ± 0.5 | 6.8 ± 0.5 |

[1]Each value represents the mean number of minutes spent in each chamber ± S.E.M. (n = 8–10).
[2]Monitored animals were injected only with saline.
[3]Animals received GVG or Saline 2.5 hours prior to receiving saline or cocaine (20 mg/kg).
[4]Significantly greater than all treatment groups, p < 0.05, ANOVA and Newman-Keuls Test.
[5]Significantly less than all treatment groups, p < 0.01, ANOVA and Newman-Keuls test.

TABLE V

| Treatment pairings[1] | Time spent in chambers (min) | |
|---|---|---|
| | Paired | Unpaired[2] |
| Saline/Saline | 7.4 ± 0.3 | 7.6 ± 0.4 |
| Saline/Cocaine | 11.6 ± 0.5[4] | 3.4 ± 0.4[5] |
| 150 mg/kg GVG[3]/Saline | 7.8 ± 0.6 | 7.2 ± 0.6 |
| 150 mg/kg GVG[3]/Cocaine | 7.9 ± 0.8 | 7.1 ± 0.8 |

[1]Each value represents the mean number of minutes spent in each chamber ± S.E.M. (n = 8–10).
[2]Monitored animals were injected only with saline.
[3]Animals received GVG or Saline 2.5 hours prior to receiving saline or cocaine (20 mg/kg).
[4]Significantly greater than all treatment groups, p < 0.05, ANOVA and Newman-Keuls Test.
[5]Significantly less than all treatment groups, p < 0.01, ANOVA and Newman-Keuls Test.

TABLE VI

| Treatment pairings[1] | Time spent in chambers (mins) | |
|---|---|---|
| | Paired | Unpaired[2] |
| Saline/Saline | 7.7 ± 0.3 | 7.3 ± 0.3 |
| Saline/Cocaine | 11.2 ± 0.6[4] | 3.8 ± 0.5[5] |
| 300 mg/kg GVG[3]/Saline | 7.2 ± 0.4 | 7.8 ± 0.4 |
| 300 mg/kg GVG[3]/Cocaine | 7.6 ± 0.7 | 7.2 ± 0.7 |

[1]Each value represents the mean number of minutes spent in each chamber ± S.E.M. (n = 8–10).
[2]Monitored animals were injected only with saline.
[3]Animals received GVG or Saline 2.5 hours prior to receiving saline or cocaine (20 mg/kg).
[4]Significantly greater than all treatment groups, p < 0.05, ANOVA and Newman-Keuls Test.
[5]Significantly less than all treatment groups, p < 0.01, ANOVA and Newman-Keuls Test.

TABLE VII

Effect of GVG and saline on the expression of cocaine-induced conditioned place preference

| Treatment pairings[1] | Drug given on test day | Time spent in chambers (min) | |
|---|---|---|---|
| | | Paired | Unpaired[2] |
| Saline/Saline | Saline | 7.5 ± 0.4[1] | 7.5 ± 0.4 |
| Saline/Saline | GVG, 75 mg/kg | 7.5 ± 0.3 | 7.5 ± 0.3 |
| Saline/Cocaine | Saline | 11.8 ± 0.5[3] | 3.2 ± 0.5 |
| Saline/Cocaine | GVG, 75 mg/kg | 10.6 ± 0.6[3] | 4.4 ± 0.9 |
| Saline/Saline | Saline | 7.8 ± 0.5[1] | 7.2 ± 0.6 |

[1]Each value represent the mean number of minutes spent in each chamber ± S.E.M. (n = 10).
[2]Monitored animals were injected only with saline.
[3]Significantly greater than all other treatment paintings, p < 0.01, ANOVA and Student Newman-Keuls test.

TABLE VIII

| Treatment pairings[1] | Drug given on test day | Time spent in chambers (min) | |
|---|---|---|---|
| | | Paired | Unpaired[2] |
| Saline/Saline | Saline | 7.1 ± 0.5 | 7.9 ± 0.5 |
| Saline/Saline | GVG, 112 mg/kg | 7.2 ± 0.3 | 7.8 ± 0.3 |
| Saline/Cocaine | Saline | 12.2 ± 0.6[3] | 2.8 ± 0.5 |
| Saline/Cocaine | GVG, 112 mg/kg | 8.1 ± 0.7 | 6.9 ± 0.6 |

[1]Each value represents the mean number of minutes spent in each chamber ± S.E.M. (n = 10).
[2]Monitored animals were injected only with saline.
[3]Significantly greater than all other treatment pairings, p < 0.01, ANOVA and Student Newman-Keuls test.

TABLE IX

| Treatment pairings[1] | Drug given on test day | Time spent in chambers (min) | |
|---|---|---|---|
| | | Paired | Unpaired[2] |
| Saline/Saline | Saline | 7.2 ± 0.2[1] | 7.8 ± 0.2 |
| Saline/Saline | GVG, 150 mg/kg | 7.7 ± 0.2 | 7.3 ± 1.1 |
| Saline/Cocaine | Saline | 11.1 ± 0.5[3] | 3.9 ± 0.4[4] |
| Saline/Cocaine | GVG, 150 mg/kg | 7.9 ± 0.3 | 7.1 ± 0.3 |

[1]Each value represents the mean number of minutes spent in each chamber ± S.E.M. (n = 10).
[2]Monitored animals were injected only with saline.
[3]Significantly greater than all other treatment pairings, p < 0.01, ANOVA and Student Newman-Keuls test.
[4]Significantly less than all other treatment pairing, p < 0.01, ANOVA and Student Newman-Keuls test.

TABLE X

| Treatment pairings[1] | Drug given on test day | Time spent in chambers (min) | |
|---|---|---|---|
| | | Paired | Unpaired[2] |
| Saline/Saline | Saline | 7.8 ± 0.5[1] | 7.2 ± 0.6 |
| Saline/Saline | GVG, 300 mg/kg | 7.3 ± 0.4 | 7.7 ± 0.3 |
| Saline/Cocaine | Saline | 12.5 ± 0.8[3] | 2.5 ± 0.6[4] |
| Saline/Cocaine | GVG, 300 mg/kg | 7.9 ± 0.5 | 7.1 ± 0.6 |

[1]Each value represents the mean number of minutes spent in each chamber ± S.E.M. (n = 10).
[2]Monitored animals were injected only with saline.
[3]Significantly greater than all other treatment pairings, p < 0.05, ANOVA and Student Newman-Keuls test.
[4]Significantly less than all other treatment pairings, p < 0.05, ANOVA and Student Newman-Keuls test.

By itself, GVG produced neither a CPP nor a conditioned aversive response. See again, Tables 3–10.

Example 3
Food-Induced Conditioned Place Preference Studies in Rodents

In this example the produce outlined in Section 3 of Material and Methods was followed. The results set forth in the Table 11 below indicate that food elicited an incentive or rewarding effect. For example, all paired values show that rodents spent more time in the chamber where food was present.

TABLE XI

Effect of GVG (150, 300 mg/kg, ip) on conditioned place preference to food

| Treatment pairings | Time spent in chambers (min) | |
|---|---|---|
| | Paired | Unpaired[2] |
| Saline/Saline | 7.3 ± 0.6 | 7.7 ± 0.6 |
| GVG/Saline | 7.5 ± 0.7 | 7.5 ± 0.7 |
| Saline/Food | 9.3 ± 0.7 | 5.7 ± 0.7 |
| GVG (150 mg/kg)/Food | 9.4 ± 0.4 | 5.6 ± 0.5 |
| GVG (300 mg/kg)/Food | 9.0 ± 0.5 | 6.0 ± 0.5 |

[1]Each value represents the mean number of minutes spent in each chamber ± S.E.M
[2]Monitored animals were injected only with saline.

The administration of 150 or 300 mg/kg of GVG did not alter the CPP response to food as shown in Table 11 despite attenuating the incentive motivational effects of cocaine in the above noted CPP experiments as shown in Tables 3–10 above.

Discussion of Experimental Results Obtained in Examples 1, 2 and 3

In previous PET studies, we showed that GVG alone reduces extracellular DA concentrations resulting in an increase in [$^{11}$C]-raclopride binding in the primate brain (Dewey, et al., 1992). In the PET studies of the present invention, GVG-induced decreases in extracellular DA levels prior to cocaine administration clearly underlie the attenuation of cocaine's effects observed in group 3 of Table 1. However, the seemingly identical values found for groups 1 and 3, combined with our previous findings using GVG alone (Dewey, et al., 1992), indicate that cocaine increased extracellular DA levels in the present invention despite GVG administration, but only to baseline values.

However, based on the CPP data presented here, this cocaine-induced return to baseline was apparently insufficient to produce incentive motivational effects. Our results indicate that cocaine produced a CPP response. In contrast, vehicle pairings did not produce a CPP response, indicating that the animals did not display a chamber preference, i.e., the apparatus is unbiased. In addition, the CPP response to cocaine was dose-dependent, with the most reliable and robust response occurring at the 20 mg/kg cocaine dose.

Administration of 112, 150, 300 mg/kg but not 75 mg/kg of GVG blocked the acquisition and expression of the CPP response elicited by cocaine. In contrast, GVG, when paired with saline, did not produce a CPP or aversive response. This indicates that the blockade of the CPP to cocaine by GVG was not related to GVG's eliciting an aversive or appetitive response by itself Our results presented in Example 2 indicated that food elicits an incentive or rewarding effect. The administration of 150 or 300 mg/kg of GVG did not alter the CPP response to food, despite attenuating the incentive effects of cocaine. This finding suggests that GVG specifically attenuates the rewarding/incentive effects of cocaine.

Example 4
Locomotor Activity and Catalepsy Studies in Laboratory Rodents

Figure 3A:
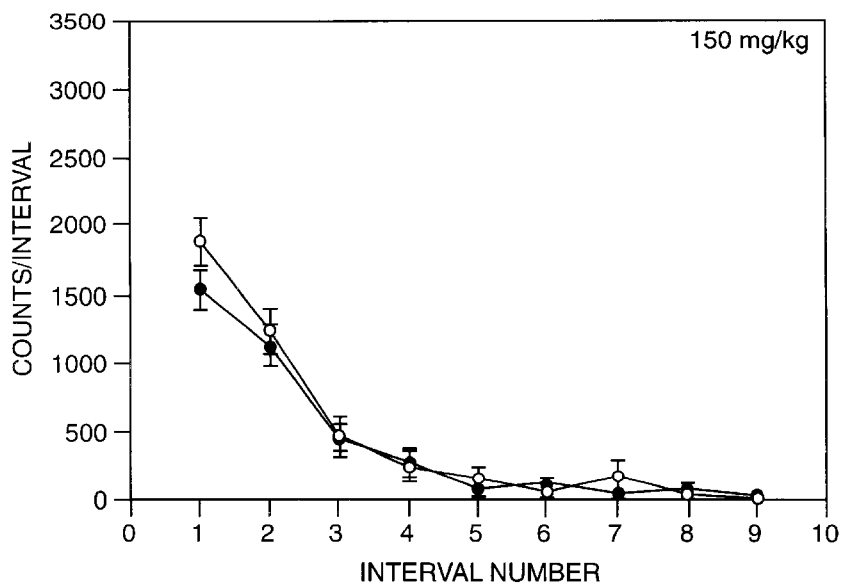
FIGS. 3A and 3B are graphs illustrating the effects of GVG on locomotor behavior as compared with saline controls.
Figure 3B:
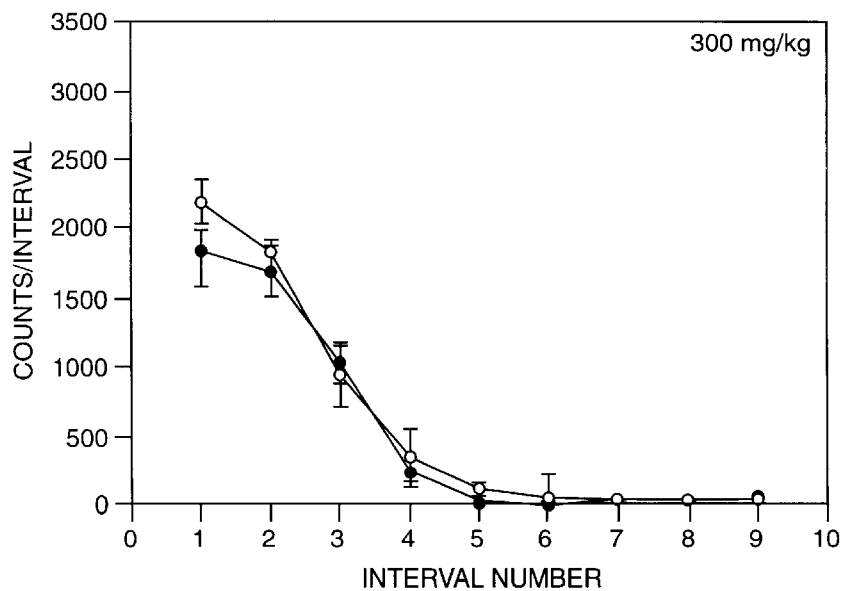

In this example the procedures outlined in Section 4 and 5 of Materials and Methods were followed. Although it is widely accepted that the CPP paradigm differentiates incentive motivational effects from motoric effects, we nevertheless assessed GVG's effects on locomotion and catalepsy in rats. We found that pretreatment with GVG at doses of 150 mg/kg or 300 mg/kg did not alter locomotor activity compared to saline pretreated controls as shown in FIGS. 3a and 3b. In addition, pretreatment with GVG at doses of 150 mg/kg or 300 mg/kg did not induce catalepsy in rats. Catalepsy duration after 300 mg/kg GVG was 1.1+0.4 seconds (n=10), which was not significantly different from 0.7+0.3 seconds (n=10) in saline-treated rats. n indicates the number of rodents which were tested.

Example 5
$^{11}$C-Cocaine levels in Rodents and Primates

In this example the procedure outlined in Section 6 of Materials and Methods was followed. In order to assess the possibility that GVG could attenuate cocaine's actions by altering its penetration into the brain, we examined the effect of saline and GVG on [$^{11}$C]-cocaine levels in the whole rat and primate brain. In rodents, the levels of [$^{11}$C]-cocaine in the brain following intraperitoneal administration of saline and 300 mg/kg GVG were 0.110±0.03 and 0.091±0.02, respectively, which did not statistically differ. In primates, the pharmacokinetic profile of labeled cocaine binding in the neostriatum was not significantly different from the baseline scan both in terms of absolute uptake as well as clearance.

Example 6

In this example, the effects of GVG on nicotine-induced changes in extracellular dopamine concentrations were measured in freely moving rats. The procedure outlined in Section 7 of Materials and Methods was followed.

A total of 8 rats were examined for each treatment pairing. Animals received 4 pairings over an 8 day period, one pairing per day.

Animals received 75 mg/kg of GVG 2.5 hours prior to receiving 0.4 mg/kg of nicotine. Animals were given GVG, then nicotine and placed in the appropriate chamber on day 1. On day 2, the animals were given GVG, then saline and placed in the appropriate chamber. The protocol on days 1 and 2 was repeated 3 additional times. Twenty four hours after the last pairing was administered, the animals were allowed free access to the entire behavioral apparatus for 15 minutes and the amount of time spent in the paired and unpaired chambers recorded using an automated device. The effects of 75 mg/kg of intraperitoneally applied GVG on acquisition of CPP to nicotine by the rats examined in this example is set forth in Table XII below.

TABLE XII

Effect of 75 mg/kg i.p. GVG on acquisition of conditioned place preference to (−)-nicotine.

| Treatment Pairings | Time spent in chambers (min)[1] | |
| --- | --- | --- |
| | Paired | Unpaired[2] |
| Nicotine 0.4 mg/kg, s.c./Vehicle[3] | 9.4 ± 0.5 | 5.6 ± 0.5 |
| 75, g/kg GVG/Nicotine, 0.4 mg/kg, s.c. | 6.4 ± 0.3[4] | 8.6 ± 0.3[5] |

[1]Each value represents the mean number of minutes spent in each chamber ± S.E.M.
[2]Monitored animals were injected only with saline.
[3]The vehicle was 1 ml/kg of 0.9% NaCl or saline solution.
[4]Significantly less than nicotine/vehicle pairing, p < 0.01, ANOVA and Student-Newman-Keuls test.
[5]Significantly greater than nicotine/vehicle pairing, p < 0.01, ANOVA and Student-Newman-Keuls test.

Figure 4:
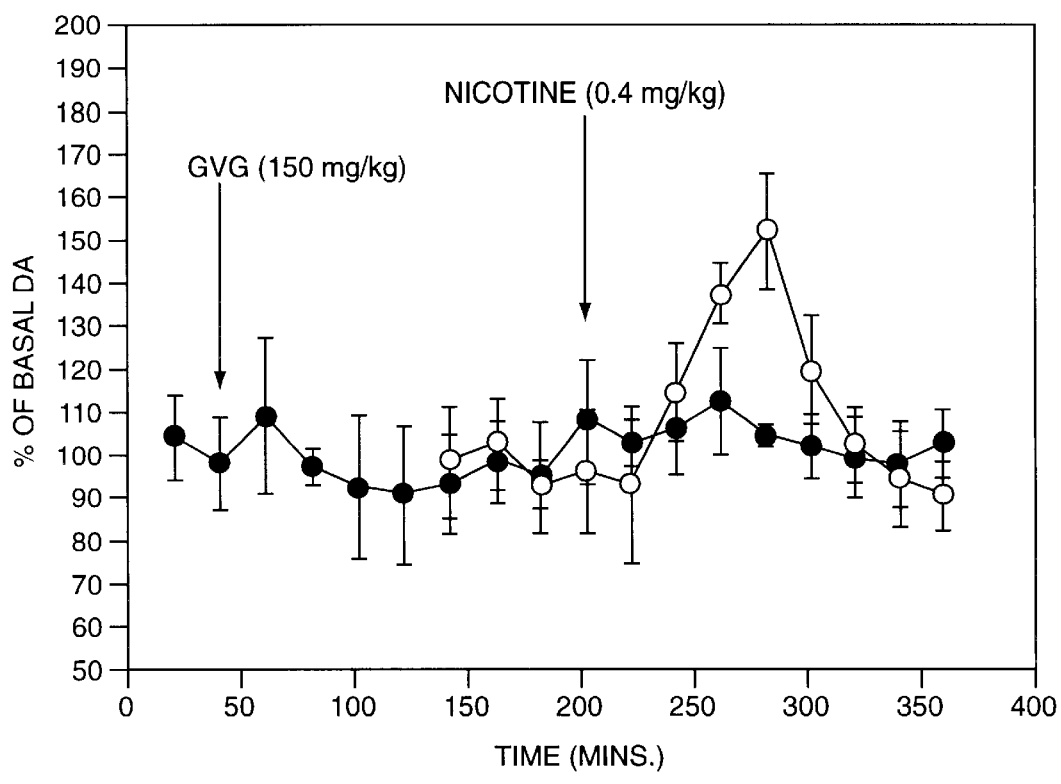
FIG. 4 is a graph illustrating the effects of GVG on nicotine-induced extracellular dopamine.

The results of a similar experiment as the one summarized in Table XII are shown in FIG. 4. FIG. 4 shows that GVG (150 mg/kg) blocks nicotine-induced increases in dopamine concentrations in freely moving rats. The open circles are control animals. The closed circles are from animals treated with GVG 2.5 hours before nicotine.

Comparative Example
Effects of Baclofen on Cocaine Use

Our results obtained in Examples 1, 2 and 3 were consistent with previous studies suggesting that the augmentation of GABAergic function can attenuate the rewarding/reinforcing actions of cocaine and other drugs of abuse. For example, it has been shown that, using the progressive ratio paradigm, the selective $GABA_B$ agonist baclofen produced a dose-dependent decrease in the break points for intravenous (i.v.) administration of cocaine in male Wistar rats, although it did not affect the rate of drug intake. These results suggested that baclofen attenuated the reinforcing effects of cocaine, as a decrease in the break point represents a decrease in the motivation to self-administer cocaine.

It has also been hypothesized that augmentation of $GABA_A$ receptor function carry attenuate cocaine self-administration, as chlordiazepoxide and alprazolam, positive allosteric modulators of the $GABA_A$ receptor complex, decreased the rate of cocaine self-administration. However, this effect is probably related to an increase in the reinforcing value of each unit dose of cocaine, as chlordiazepoxide will increase the break point for cocaine self-administration on a progressive ratio schedule.

The findings with baclofen were reinforced by a recent study from the same laboratory indicating that acute pretreatment of rats with baclofen (1.25–5 mg/kg i.p.) will suppress self-administration of cocaine in a discrete trials paradigm for at least four hours without significantly altering responding for food reinforcement. Microinjection of baclofen into the ventral tegmental area ipsilateral to a stimulating electrode in the lateral hypothalamus of rats produced a rightward shift of the rate-current intensity curve, indicating that baclofen attenuated the rewarding value of the electrical stimulation. However, baclofen did not affect the maximal responding rate for electrical brain stimulation reward or non-reinforced performance levels, suggesting that baclofen's action was not related to alterations in motor performance/dexterity.

A recent study demonstrated that GVG produced a dose-dependent increase in brain stimulation reward thresholds in male F344 rats (Kushner et al., 1997b), without significant effects on motor performance. The decrease in brain stimulation reward thresholds produced by 2.5 and 5 mg/kg of intraperitoneally administered cocaine was significantly antagonized by 400 mg/kg dose of GVG.

Finally, the CPP response elicited by morphine (8 mg/kg) was significantly attenuated by microinjection of baclofen (0.1–1 nmol) into the ventral tegmental area and this effect was antagonized by the $GABA_B$ antagonist 2-hydroxysaclofen. Thus, despite using different paradigms to assess reward/reinforcement, these studies indicate that activation of $GABA_B$ receptors attenuated the appetitive value of cocaine, morphine and electrical brain stimulation reward.

Previously, it was reported that pretreatment with the GABA-mimetic compound progabide (which augments GABA levels in the brain via its metabolism to GABA), which alone does not produce conditioned place preference or aversion, did not alter the CPP response to 1.5 mg/kg i.p. of amphetamine. However, it is difficult to compare this finding to the present invention as there were differences in rat strains, GABAergic compounds and drugs used to elicit CPP. It should also be noted that progabide was only present for 35 minutes. Since it has been shown that the maximal increase in GABA levels in the brain following systemic progabide occurs four-six hours after injection, GABA levels were not at their maximum during the determination of amphetamine-induced CPP.

Given the evidence suggesting that augmentation of dopaminergic function in the mesolimbic system plays a role in mediating the rewarding/reinforcing effects of cocaine, the abolition of the CPP response to cocaine by GVG may be related to an alteration of dopaminergic activity/function. This hypothesis is supported by our in vivo microdialysis study indicating that acute (300 and 500 mg/kg i.p.) or repeated administration (100, 300, and 500 mg/kg i.p.) of GVG produced a significant dose-dependent decrease in the elevation of extracellular DA levels in the NACC and striatum produced by 20 mg/kg i.p. of cocaine (Dewey, et al., 1998). At the same time, it is unlikely that an alteration in the sensitivity of DA receptors following GVG administration is responsible for its attenuation of cocaine's action, because it is known that the repeated administration of GVG does not alter $D_1$ or $D_2$ receptor sensitivity in the rat striatum. However, no evidence exists regarding GVG's effects on other DA receptors ($D_3$, $D_4$ and $D_5$). Alternatively, it is possible that cocaine could alter $GABA_B$ receptor function, thereby potentially altering the release of neurotransmitters such as DA and this could be antagonized by GVG via elevation of GABA levels and consequent stimulation of $GABA_B$ receptors.

It has also been shown that the repeated administration of cocaine diminishes the effectiveness of presynaptic $GABA_B$ auto and hetero-receptors on lateral septal nucleus neurons in rat brain slices. This may lead to a disinhibtory action and enhanced neurotransmitter release. It is also possible that baclofen could attenuate the action of DA and this would attenuate cocaine's actions. This is indirectly supported by the findings of Lacey et al. (1988), showing that in intracellular recordings from rat substantia nigra zona compacta neurons, the outward currents elicited by DA were occluded by maximal currents produced by baclofen.

Several interpretations of the present results are possible. First, it is possible that GVG could increase the metabolism of cocaine, thereby decreasing the amount which reaches the brain and subsequently diminishing its neurochemical effects and ultimately its behavioral actions. However, this is unlikely as brain levels of $^{11}$C-cocaine were not significantly altered in rats or primates pretreated with GVG (300 mg/kg). Furthermore, cocaine is primarily metabolized by plasma cholinesterases whereas GVG is excreted primarily unchanged in the urine, making a pharmacokinetic interaction unlikely.

It has been reported that drugs which augment GABAergic function can produce sedation and ataxia. Consequently, it is reasonable to postulate that GVG, by producing such adverse behavioral effects, may non-specifically antagonize cocaine's action. However, the results in the present study indicate that GVG does not produce catalepsy or significantly alter locomotor activity, making this hypothesis untenable. Furthermore, the examples discussed above show that GVG does not produce conditioned place aversion, indicating that its antagonism of cocaine's action is not the result of a counterbalancing aversive action. In addition, GVG does not elicit CPP alone, indicating that it is not shifting the preference of animals from the cocaine-paired to the GVG-paired environment.

It has been shown that GVG administration can alter food consumption in rats. Based on this, it is possible that GVG may decrease or attenuate the hedonic value of natural rewards, as well as that elicited by cocaine. However, the present study shows that neither 150 nor 300 mg/kg of GVG alters CPP to food.

There is evidence indicating that behavior in the conditioned place preference (CPP) paradigm depends upon both the affective and memory-improving properties of the reinforcers under test. Therefore, one might argue that GVG's blockade of the expression and acquisition of cocaine-induced CPP is the result of GVG interfering with the association of cocaine-induced positive incentive value with the appropriate stimuli by interfering with memory. Indeed, it is known that certain drugs which augment GABAergic function can impair memory. However, GVG does not affect place conditioning for food, suggesting that this hypothesis cannot explain GVG's antagonism of cocaine's action in the CPP paradigm.

It has been found that the 112, 150 and 300 mg/kg doses of GVG antagonize the acquisition and expression of cocaine-induced CPP. In contrast, GVG did not elicit a CPP or conditioned place aversion response, indicating that GVG does not antagonize cocaine's action by producing a CPP response alone or by attenuating CPP by producing an aversive effect. Furthermore, GVG did not elicit catalepsy and did not alter the incentive value of food. There is evidence that cocaine-related stimuli or cues will reinstate drug-seeking behavior and craving in detoxified cocaine addicts, thereby leading to relapse. The expression of the CPP to cocaine, determined in the absence of cocaine, is antagonized by GVG. These results indicate that the craving experienced by cocaine addicts can be attenuated by GVG.

Dopaminergic transmission in the NACC has been specifically implicated in the reinforcing properties of cocaine. In the PET studies discussed above, measurements were made in the corpus striatum rather than the NACC. Although DA neurotransmission in the corpus striatum has not been implicated in cocaine reward and reinforcement, the effects of cocaine on extracellular DA levels are qualitatively similar in both areas. In addition, our in vivo microdialysis studies demonstrated the ability of GVG to attenuate cocaine-induced increases in extracellular DA levels to a similar extent in both areas (Dewey, et al., 1997; Morgan and Dewey, 1998).

In the present invention, two different species of rodents and primates were used to conduct imaging and behavioral experiments. However, the mesocorticolimbic DA system is neuroanatomically and neurophysiologically homologous in both species. In addition, the biochemical effects of cocaine on extracellular DA, measured by in vivo microdialysis techniques, are similar in both species, and both rodents and primates readily self-administer cocaine (Morgan, et al., 1998).

Based on the experimental results of the present invention it is submitted that the blockade of the behaviors in the CPP paradigm was due to an attenuation of cocaine's effects on brain DA secondary to the GVG-induced increases in GABAergic inhibition of the mesocorticolimbic DA system.

GVG offers the conceptual advantage of blocking cocaine's incentive motivational and biochemical effects on brain DA by irreversiby inhibiting GABA-T, making the relatively slow de novo synthesis of this enzyme the rate determining step in reversing the inhibition of cocaine's effects. A recent case report of a cocaine abuser suggests that gabapentin, an anticonvulsant that also potentiates GABAergic transmission via unknown mechanisms, attenuated cocaine withdrawal and craving. Taken together, these data indicate that drugs selectively targeted at the GABAergic system can be beneficial for the treatment of cocaine addiction. More specifically, GVG-induced GABA-T inhibition, which produces an increase in extracellular brain GABA levels, represents an effective drug and novel strategy for the treatment of cocaine addiction.

Example 7

The phenomenon of sensitization is observed with virtually all drugs of addiction. Sensitization is believed to play a role in the etiology of addiction. In this example, the effect of saline and 150 mg/kg i.p. of GVG on the expression of cocaine-induced stereotypic behavior following a sensitizing regimen of cocaine was measured in ten freely moving rats.

Animals received 15 mg/kg i.p. of cocaine and stereotypy was determined in standard locomotor cages. For 6 consecutive days, animals received 15 mg/kg i.p. of cocaine once a day in their home cages. Eight days later, animals were rechallenged with 15 mg/kg i.p. of cocaine and stereotypy was determined. A five point rating scale was used to assess stereotypy and the rater was blind to the treatment received by each animal. It was noted that GVG abolished the expression of cocaine-induced sensitization at a dose of 150 mg/kg i.p., when administered 2.5 hours prior to the cocaine challenge. The results are shown in Table XIII below.

TABLE XIII

Effect of saline and 150 mg/kg i.p. of GVG on the expression of cocaine-induced stereotypies following a sensitizing regimen of cocaine.

| Stereotypy score on Day 1 | Treatment 2 hrs. before measuring Stereotypy Score | Stereotypies on Day 15 |
|---|---|---|
| 2.5 ± 0.4 | 1 ml/kg i.p. of 0.9% NaCl | 4.1 ± 0.5* |
| 2.9 ± 0.4 | 150 mg/kg i.p. of GVG | 2.3 ± 0.6 |

*Significantly greater than Day 1, $p < 0.05$, Student's test

The next experiments were designed to determine the effects of GVG on nicotine-induced increases in NACC DA as well as on behaviors associated with this bio-chemical effect. Specifically, this was accomplished by: 1) using in vivo microdialysis in freely moving naive and chronically-nicotine treated animals to measure the effects of GVG and nicotine on extracellular NACC DA; 2) using positron emission tomography (PET) to measure the effect of GVG on nicotine-induced decreases in $^{11}$C-raclopride binding in the striatum of anesthetized, female baboons and 3) examining the effect of GVG on nicotine-induced CPP.

Example 8

Effects of GVG on nicotine-induced increases in NACC DA
1. Microdialysis studies in Rodents In this example, nicotine was used as the addictive drug. In animals of (Group 1), nicotine (0.4 mg/kg, sc) was administered 2.5 hours after GVG (75, 90, 100, or 150 mg/kg , i.p). In a separate series of experiments (Group 2) animals were treated for 21 days with nicotine (0.4 mg/kg , s.c., twice daily). On the day of the study, GVG (100 mg/kg) was administered either 2.5, 12 or 24 hours prior to nicotine (0.4 mg/kg , s.c.) challenge. In all studies, animals were placed in the microdialysis bowls the night before the experiment and artificial cerebrospinal fluid (ACSF) was perfused through the microdialysis probes at a flow rate of 2.0 µl/min. At the end of each study, animals were sacrificed and their brains were removed and sectioned for probe placement verification.

In Group 1 animals, nicotine increased extracellular DA concentrations in the NACC by approximately 100%, 80 minutes following administration (FIG. 5A). That is, DA levels were elevated to approximately 200% of basal levels. DA returned to basal levels approximately 160 minutes following administration. GVG in a dose-dependent fashion inhibited this increase as shown in FIG. 5A. At 75 mg/kg, GVG had no effect on nicotine-induced increases in DA while at 90 mg/kg, GVG inhibited DA increases by approximately 50% and at 100 mg/kg, it completely abolished any DA increase. The highest dose of 150 mg/kg completely abolished the effects as well (data not shown). Of particular note is the finding that at the three higher doses (90, 100, or 150 mg/kg) GVG lowered basal DA levels prior to nicotine administration. The lowest dose (75 mg/kg) had no effect on basal DA levels and subsequently no effect on nicotine's ability to elevate extracellular NACC DA.

Figure 5B:
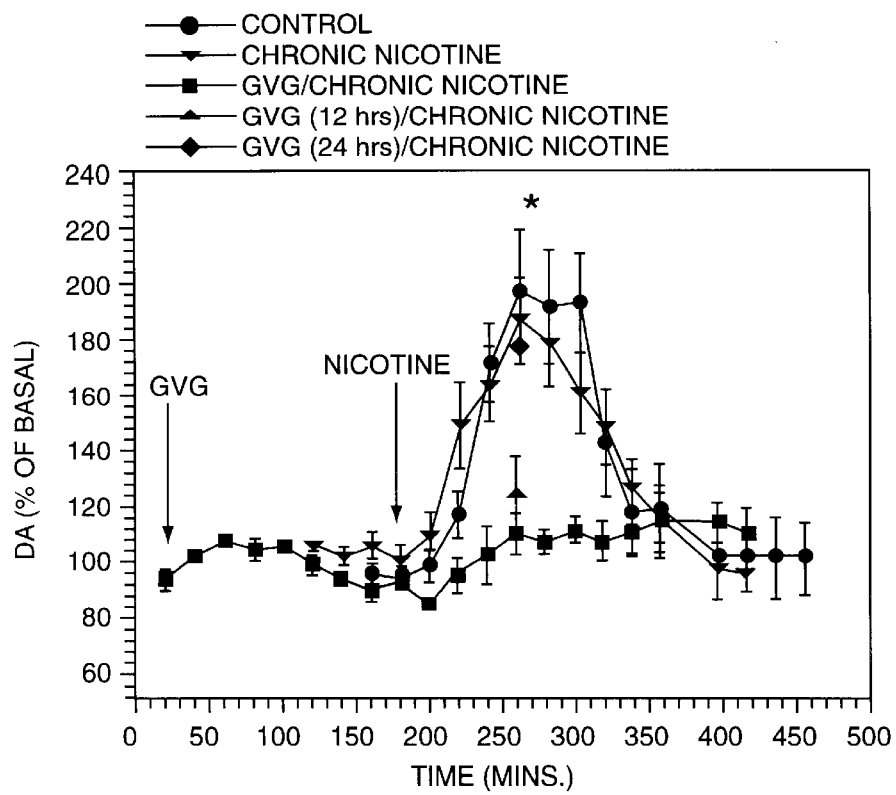

In Group 2 animals, nicotine increased extracellular NACC DA levels within the same time period and to the same extent measured in Group 1 animals (approximately 100% above baseline, FIG. 5B). Similar to our findings in Group 1, when administered 2.5 hours prior to nicotine administration, GVG (100 mg/kg) completely abolished nicotine-induced increases in extracellular DA. However, when administered 12 hours prior to challenge, nicotine increased extracellular DA levels approximately 25% above baseline values (FIG. 5B). In Group 2 animals that received GVG 24 hours prior to nicotine challenge, extracellular DA levels increased to values similar to those measured in control animals (FIG. 5B). Consistent with our previous findings (Dewey, et al., 1997), GVG did not alter gross locomotor activity during the 2.5 hour pretreatment interval. However, nicotine increased gross locomotor activity in all animals regardless of the dose of GVG they received.

Example 9

2. Nicotine-induced CPP in Rodents

Description of CPP Apparatus

The CPP apparatus was made entirely of plexiglass, except for the floor in one of the pairing chambers, which was made of a stainless steel plate with holes (0.5 mm in diameter) spaced 0.5 mm from edge to edge. The two pairing chambers differed in visual and tactile cues. One chamber was entirely light blue with the stainless steel floor and the second chamber was light blue with horizontal black stripes (2.5 cm wide) spaced 3.8 cm apart with a smooth plexiglass floor. The two pairing chambers were separated by a third, neutral connecting tunnel (10×14×36 cm) with clear plexiglass walls and a plexiglass floor. The visual and tactile cues were balanced such that no significant side preference was exhibited by animals prior to conditioning.

The effect of GVG on the expression of CPP in Rodents

The conditioning procedure consisted of 20 sessions carried out consecutively over 20 days. The first three sessions were habituation sessions, during which the animals were handled for 5 minutes per day and exposed to the sights and sounds of the test room. This was followed by 16 sessions of 8 pairings with 1) vehicle/vehicle (1 ml/kg i.p. 0.9% saline, n=10 animals) or 7 saline-nicotine (0.4 mg/kg s.c.) groups with 10 animals in each group. Half the animals in any test group received nicotine before exposure to the blue chamber and the other half receive saline before exposure to the blue and black striped chamber. The animals that received vehicle or nicotine were injected and confined to the appropriate compartment for 30 minutes via guillotine plexiglass doors to block access to the rest of the chamber. The final session (day 20) was a test session, in which animals received one of the following treatments 30 minutes before the experiment: 1) saline or 2) GVG (18.75, 37.5, 75 or 150 mg/kg i.p.). The entrances to both pairing chambers were opened, and the animals were allowed to freely move between the 3 chambers for 15 minutes. The amount of time spent in each chamber was recorded using an automated infrared beam electronically coupled to a timer.

The effect of GVG on the acquisition of CPP

The animals were habituated as described above. Animals were given either saline or GVG (37.5 and 75 mg/kg i.p.) 2.5 hours before the animals received nicotine. Subsequently, the animals were then placed into the appropriate chamber for 30 minutes. This was repeated for 8 pairings over a 16 day period. On the test day, animals were placed in the CPP apparatus and allowed free access to the all of the CPP chambers and the amount of time spent in chamber was recorded.

The administration of saline did not produce a chamber preference. However, nicotine (0.4 mg/kg s.c.) produced a statistically significant and reliable CPP response where animals spent 9.6+0.6 mins on the paired (nicotine) side compared with 5.4+0.6 mins on the unpaired (saline) side (Table XIV and XV). Statistical analysis of the expression data indicated a treatment effect (F(5, 50)=21.6, p<0.001). Post hoc analysis revealed that GVG at doses of 18.75, 37.5, 75.0, or 150 mg/kg but not saline, abolished the expression phase of nicotine-induced CPP (Table XIV).

Analysis of the acquisition data indicated a treatment effect (F(3,32)=11.8, p<0.05). Post hoc analysis indicated that GVG (37.5 mg/kg) did not significantly block the acquisition of the nicotine-induced CPP (Table XV). In contrast, at a dose of 75 mg/kg, GVG significantly blocked the acquisition phase of nicotine-induced CPP (Table XV).

TABLE XIV

Effect of saline and GVG on expression of conditioned placed preference response to 0.4 mg/kg s.c. of (−) nicotine

| Treatment Pairings | Drug given on test day | Time Spent in chambers (min) | |
|---|---|---|---|
| | | Paired | Unpaired |
| Saline/Saline | Saline[2] | 7.4 ± 0.3[1] | 7.6 ± 0.3 |
| Saline/Nicotine | Saline | 9.6 ± 0.6 | 5.4 ± 0.6 |
| Saline/Nicotine | GVG, 18.75 mg/kg[3] | 7.5 ± 0.7* | 7.5 ± 0.7 |
| Saline/Nicotine | GVG, 37.5 mg/kg | 6.8 ± 1.0** | 8.2 ± 1.0 |
| Saline/Nicotine | GVG, 75 mg/kg | 6.4 ± 0.3** | 8.6 ± 0.3 |
| Saline/Nicotine | GVG, 150 mg/kg | 5.0 ± 0.9** | 10.0 ± 0.9 |

[1]Each value represents the mean number of minutes spent in each chamber ± S.E.M. A total of 8–10 rats were examined for each treatment pairing. All animals received 8 pairings with nicotine and saline prior to the test day. On the test day, animals received either saline or GVG 2.5 hours before being placed into the CPP apparatus.
[2]Saline was 1 ml/kg s.c. of 0.9% saline.
*Significantly less than Saline/Nicotine pairing with saline on test day, P < 0.05, ANOVA and Student-newman-Keuls test.
**Significantly less than Saline/Nicotine pairing with saline on test day, P < 0.01, ANOVA and Student-Newman-Keuls test.

TABLE XV

Effect of saline and GVG on acquisition of conditioned place preference response to 0.4 mg/kg s.c. of (−)-nicotine

| Treatment Pairings | Time spent in chambers (min) | |
|---|---|---|
| | Paired | Unpaired |
| Saline/Saline[2] | 7.3 ± 0.3[1] | 7.7 ± 0.3 |
| Saline/Nicotine | 9.6 ± 0.6[1] | 5.4 ± 0.6 |
| Nicotine/GVG, 37.5 mg/kg i.p. | 8.8 ± 0.5 | 6.2 ± 0.5 |
| Nicotine/GVG, 75 mg/kg i.p. | 6.9 ± 0.9* | 8.1 ± 0.9 |

[1]Each value represents the mean number of minutes spent in each chamber ± S.E.M. A total of 8–10 rats were examined for each treatment pairing. Animals were pretreated with either saline, 37.5 or 75 mg/kg i.p. of GVG and 2.5 hours later, each animal received 0.4 mg/kg s.c. of nicotine, except for one group, which received saline followed by saline treatment (saline/saline pairing). Eight pairings were performed with each animal.
[2]The saline was 1 ml/kg s.c. of 0.9% saline.
*Significantly less than Saline/Nicotine pairing with saline on test day, P < 0.05, ANOVA and Student-Newman-Keuls test.

Primate PET studies

Adult female baboons (n=16) (Papio anubis, 13–18 kg) were used for all imaging studies and carbon-11 labeled raclopride ($^{11}$C-raclopride). Animals were placed into 5 groups as detailed in Table XVI. Control animals (Group 1) received two injections of $^{11}$C- raclopride without any drug intervention in order to determine the test/retest variability of the measurement. These data have been reported previously (Dewey et al., 1998). Group 2 animals received GVG alone (300 mg/kg) 2.5 hours prior to the second injection of $^{11}$C-raclopride. Like Group 1 animals, these data have been reported previously (Dewey, et al., 1992). Group 3 animals received nicotine alone (0.3 mg total, approximately 0.02 mg/kg) 30 minutes prior to the second injection of $^{11}$C-raclopride. In the combined GVG/nicotine studies, GVG was administered intravenously (i.v.) at doses of 100 (Group 4) or 300 mg/kg (Group 5) 2.5 hours prior to nicotine administration. Nicotine (0.3 mg total, i.v.) was administered 30 minutes prior to the second injection of $^{11}$C- raclopride. Arterial blood samples were obtained throughout the study and selected plasma samples were analyzed for the presence of unchanged $^{11}$C-raclopride. Animals were not removed from the gantry between isotope injections. Data analysis was performed using the Logan method as detailed previously (Logan, et al., 1990).

Each primate (n=16) received two $^{11}$C-raclopride injections. The first served as a baseline for the second that followed GVG, nicotine, or both. Test/retest primates (n=7, Group 1, Table XVI) received placebo (0.9% saline, 1 ml/kg) 30 mins prior to the second radiotracer injection in order to determine the test/retest variability of the method. All remaining primates (n=9) received a systemic injection of GVG, nicotine or both prior to the second [$^{11}$C]-raclopride injection.

As reported previously (Dewey, et al., 1998), the test/retest mean distribution volume (DV) ratio variability of labeled raclopride in the primate striatum was slightly greater that 7% (Table XVII). GVG administration (300 mg/kg, Group 2) significantly increased the mean DV ratio by 18% (Table XVII). These data are consistent with microdialysis studies demonstrating that GVG dose dependently decreases extracellular DA in freely moving animals. Nicotine administration (Group 3), however, produced the opposite effect of GVG and significantly reduced the mean DV ratio by 12% (Table XVII). This is again consistent with our microdialysis data demonstrating that nicotine increases extracellular DA in freely moving animals. When administered sequentially, GVG (100 mg/kg, Group 4) abolished the decrease in the mean DV ratio produced by nicotine alone (Group 3). At this dose of GVG, the mean DV ratio was similar to the test/retest value obtained in Group 1 animals (9%, Table XVII). However, when administered at a dose of 300 mg/kg (Group 5), the mean DV ratio for labeled raclopride was significantly higher (15%) than the test/retest values and was in fact, similar to the values obtained in Group 2 animals that received GVG alone (Table XVII).

It was noted that GVG, nicotine or both did not alter the rate of systemic metabolism of labeled raclopride nor the regional distribution of the radiotracer. Recovery from each study was unremarkable.

TABLE XVI

Groups for Primate PET Studies

| Group | Condition |
|---|---|
| 1 | Test/Retest (no challenge) |
| 2 | GVG (300 mg/kg) |
| 3 | Nicotine (0.3 mg) |
| 4 | GVG (100 mg/kg), Nicotine (0.3 mg) |
| 5 | GVG (300 mg/kg), Nicotine (0.3 mg) |

TABLE XVII

Effects of Drug Challenge on the Mean DV Ratio

| Group | % Change in Mean DV Ratio |
|---|---|
| 1 | 7.16 ± 1.2 |
| 2 | 18.8 ± 3.2 |
| 3 | −12.3 ± 2.6 |
| 4 | 9.45 ± 2.1 |
| 5 | 15.1 ± 2.8 |

Discussion of Experimental Results Obtained in Example 9

In this example, we demonstrated that nicotine (0.4 mg/kg s.c.) increased NACC DA by approximately 100% (or 200% above baseline) in freely moving animals approximately 80 minutes following administration. Previous microdialysis studies have reported that nicotine administration at doses of 0.6 or 0.8 mg/kg (s.c.) produced a 220% and 179% increase in extracellular DA levels in the NACC, respectively, (Di Chiara and Imperato, 1988; Imperato et al., 1986; Brazell et al., 1990). Although not directly comparable, our results are clearly in line with these earlier findings. Furthermore, in our animals exposed chronically to nicotine, a nicotine challenge produced a 90% increase in extracellular NACC DA levels. This finding is consistent with previous data indicating that chronic nicotine administration does not produce tolerance or sensitization to an acute challenge with nicotine (Damsma et al., 1989).

With respect to our findings using GVG, we demonstrated that it dose-dependently inhibited nicotine-induced increases in NACC DA in both naive and chronically nicotine treated animals. This is the first study to report such an action of GVG. At a dose of 75 mg/kg, GVG had no effect as nicotine increased extracellular DA by nearly 200% while a dose of 90 mg/kg produced an inhibition of nearly 50%. At the two highest doses examined (100 and 150 mg/kg) GVG completely abolished nicotine-induced increases in extracellular NACC DA levels. Previously, we demonstrated that an acute injection of GVG (300 mg/kg i.p) produced a 25% decrease in cocaine induced increases in NACC DA (Dewey et al., 1998). However, chronic treatment with GVG, at a similar dose, produced a greater inhibition (Morgan and Dewey, 1998). Together these data show that the dose of GVG needed to significantly attenuate drug-induced increases in NACC DA levels is dependent not only on the challenge drug used (e.g., cocaine, nicotine), but also on the dose at which the challenge drug is administered.

The present data further demonstrates that the effectiveness of GVG is related to its dose dependent ability to lower basal DA concentrations prior to drug challenge. For example, the 75 mg/kg dose had no effect on basal DA and on nicotine-induced increases in DA. However, at a dose of either 90 or 100 mg/kg, GVG lowered basal DA levels and reduced by 50% or abolished the effects of nicotine, respectively. Therefore, it appears that the dose-dependent attenuation of either nicotine or cocaine-induced increases in NACC DA is due to a pre-lowering of basal DA concentrations, subsequent to an increase in endogenous GABA produced by GVG. This is consistent with data indicating that augmentation of GABAergic function reduces DA in the NACC.

In an extension of our previous work with GVG and cocaine, we examined the temporal course of GVG's effects on nicotine-induced increases in NACC DA in animals chronically treated with nicotine for 21 days. When administered 2.5 hours prior to nicotine at a dose of 100 mg/kg, GVG completely abolished drug-induced increases in NACC DA. However, when administered at the same dose 12 hours prior to challenge, nicotine increased extracellular DA by approximately 25%.

GVG had no effect on nicotine-induced increases in NACC DA, when it was administered 24 hours prior to nicotine challenge at the same dose. Clearly, our microdialysis and behavioral data show that even small changes in GABA-T inhibition produced by increasing doses of GVG have a profound effect on the inhibition of nicotine-induced elevations in NACC DA and CPP, respectively.

These data are particularly interesting in light of the synthesis rate of GABA-T, the half-life of GVG in the rodent brain, the duration of the effect on GABA, and the sharp dose response curve detailed here. Previous findings demonstrate that the biologic half-life of GABA-T in the rodent brain is 3.4 days while the half-life of GVG in the brain is approximately 16 hours. In addition, total brain GABA levels do not begin to decrease until 24 hours following acute GVG administration (Jung, et al., 1977). The disparity between the sustained brain GABA levels measured 24 hours following a single dose of GVG and the normal response to a nicotine challenge observed at the same time point suggests that GABAergic inhibition of the mesotelencephalic reward pathway may not be a simple reflection of total brain GABA levels. That is, while total brain GABA levels are still significantly elevated 24 hours following an acute dose of GVG, small functional differences in specific pathways may be masked by these global measurements. Finally, it is conceivable that GABA receptors have become desensitized to GABA over the 24 hour period, however, we are unaware of any evidence in the GABA system that would support such an hypothesis.

In the present study, we demonstrated that 8 saline-nicotine pairings produced a reliable CPP response. Our results are in agreement with previous studies indicating that nicotine (0.1–1.2 mg/kg s.c.) produces a dose-dependence in the CPP response of male Sprague-Dawley animals (Fudala et al., 1985; Fudala and Iwamoto, 1986). We have also shown that Lewis, but not F344 animals, show a CPP response to nicotine after 10 pairings (Horan et al., 1997). However, a previous report has shown that 4 nicotine-vehicle pairings did not elicit a CPP response in male hooded animals (Clarke and Fibiger, 1987). Thus, it appears that nicotine-induced CPP may be species dependent, although this may be confounded by the fact that the studies quoted utilized a different number of pairings. The nicotine-induced CPP response reported in the present study is consistent with the notion that nicotine produces a positive effect on incentive motivational behavior.

This data, for the first time, demonstrates that GVG can block the biochemical and behavioral effects of nicotine using the CPP paradigm. The CPP data clearly indicate that at a dose as low as 18.75 mg/kg, GVG abolishes the expression of the CPP response produced by nicotine. Our data also indicated that a dose of 75 mg/kg, but not 37.5 mg/kg, blocked the acquisition of the CPP response to nicotine. Based on these dose findings, the dose of GVG needed for the treatment of smoking cessation can be a total of 250–500 mg a day (compared with 2–4 grams/day for epilepsy), a range considerably lower than that given to epileptics.

The effects of GVG on nicotine-induced CPP are unlikely to be related to its producing a rewarding or aversive effect as we have previously shown that GVG alone (75–300 mg/kg i.p.) does not produce CPP or aversion (Dewey et al., 1998). Furthermore, it is unlikely that GVG abolishes nicotine's behavioral actions by interfering with memory or locomotor activity as GVG does not block food reward or locomotor activity at doses as high as 300 mg/kg (Dewey et al., 1998).

Finally, it has been shown that GVG is not self-administered by rhesus monkeys and animals withdrawn from chronic GVG treatment do not exhibit withdrawal signs or symptoms (Takada, and Yanagita, 1997). Thus, GVG, unlike other drugs used in the pharmacotherapy of certain addictions (e.g. methadone, antabuse), is itself not addicting and does not produce significant aversive effects.

The attenuation of the acquisition of the CPP response to nicotine by GVG can be interpreted as a decrease in the positive incentive value of nicotine. These data show that GVG decreases the likelihood that an animal will acquire the association of a positive incentive effect following nicotine administration. Interestingly, our results indicated that the dose of GVG required to block the expression phase of the CPP response produced by nicotine was ¼ of the amount needed to block the acquisition of the CPP response. This finding is congruent with our previous data indicating that a higher dose of GVG was required to block the acquisition, as opposed to the expression of CPP to cocaine (Dewey et al., 1998). The explanation for this difference is unknown. Since GVG attenuates the expression of the CPP response to nicotine, this demonstrates that GVG is decreasing the drug-seeking behavior of the animal as the animal has already acquired the positive incentive value of the drug.

Thus, our data shows that GVG can be more effective in blocking the craving for nicotine than it is at blocking the positive incentive value or rewarding action of nicotine. Finally, at the highest dose tested, 150 mg/kg, GVG produced a significant aversive response on the test day (Table XV) where animals spent 5.0+0.9 on the paired (nicotine) side and 10.0+0.9 minutes on the unpaired (saline) side. These data suggest that there might be a ceiling effect at which GVG in high doses becomes aversive in animals treated with nicotine and tested in a drug-free state. These data may have implications in developing the dose limits to be tested in human clinical trials.

Based on our knowledge of the CPP paradigm, our data support the following results. In the CPP paradigm, animals are tested, in a drug-free state, to determine whether they prefer an environment in which they previously received nicotine as compared to an environment in which they previously received saline. If the animal, in a drug-free state, consistently chooses the environment previously associated with nicotine, the inference is drawn that the appetitive value of nicotine was encoded in the brain and is accessible in the drug-free state (Gardner, 1997). Indeed, on the test day, the approach and association of the animals with the drug-paired side can be considered drug-seeking behavior. In essence, environmental stimuli and other cues that were previously neutral or lacked salience have through repeated pairings with nicotine, become salient. Subsequently, when the animals are re-exposed to these cues, a CPP response is produced, i.e. the cues can elicit the drug effect. Thus, drug-related cues produce a Pavlovian conditioned response.

This is critical as it is known that non-pharmacologic factors, in addition to pharmacologic ones, play a role in mediating the incentive value of drugs of addiction (Jarvik and Henningfield, 1988). In fact, it has been demonstrated clinically that in detoxified addicts, exposure to stimuli that were previously associated with drug use, can elicit relapse (Childress et al., 1986a,b; Childress et al., 1988; Ehrman et al., 1992; O'Brien et al., 1992; Wikler, 1965). Thus, these data show that since GVG blocks the expression of the nicotine-induced CPP response, then GVG blocks the craving or seeking of nicotine. Therefore, GVG is effective in the treatment of individuals who have the desire to stop smoking cigarettes. These data further show that GVG is effective in abolishing the expression of the CPP response to nicotine and can attenuate craving in the face of environmental cues previously associated with smoking.

Our primate PET data are consistent with previous findings using multiple pharmacologic challenges that demonstrate $^{11}$C-raclopride binding is sensitive to both increases and decreases in synaptic DA (Dewey, et al., 1993; Seeman, et al., 1989). As evidenced in Group 3 animals (Table XVII), the mean DV ratio was consistently decreased relative to baseline values following nicotine administration. This decrease exceeded the test/retest variability of labeled raclopride and is less than the decrease measured with GBR-12909 (Dewey, et al., 1993) or scopolamine (Dewey, et al., 1993). Pretreatment with GVG at a dose of 100 mg/kg 2.5 hours prior to nicotine produced a mean DV ratio similar to Group 1 animals (Table XVII). However, when the dose of GVG was increased to 300 mg/kg, the mean DV ratio was elevated to values consistent with Group 2 animals. These data show that the lower dose of GVG produced a decrease in synaptic DA roughly equivalent to the increase produced by nicotine while the higher dose of GVG produced a decrease that far exceeded nicotine's ability to increase DA. Our microdialysis studies support these data that higher doses of GVG produce a greater decrease in extracellular DA in freely moving animals.

The microdialysis and PET findings combined with the CPP data show that increases in DA in the NACC alone underlie the addictive liability of drugs of abuse. First, these data, combined with the above data for cocaine, show that in vivo microdialysis studies or PET measurements of endogenous DA alone is not necessarily predicative of the efficacy of drugs used to treat diseases thought to be neurotransmitter-specific in nature. Second, both the microdialysis data and the PET data clearly demonstrate that at a dose of 100 mg/kg, GVG completely blocked nicotine-induced increases in NACC DA levels, whereas a dose of 75 mg/kg had no effect. In contrast, GVG, at a dose as low as 18.75 mg/kg, completely abolished the expression phase of nicotine-induced CPP while it took a dose of 75 mg/kg to abolish the acquisition phase.

Based upon the dose-response curve obtained from the microdialysis data, GVG at a dose of 18.75 mg/kg would not be expected to have any effect on nicotine-induced increases in NACC DA. Furthermore, a similar effect was noted using cocaine where a dose of 300 mg/kg of GVG reduced cocaine-induced increases in NACC DA levels by 25%, while a dose of 150 mg/kg completely abolished the expression and acquisition phase of cocaine-induced CPP (Dewey, et al., 1997; 1998).

Together, these data suggest at least two plausible and perhaps combined explanations. First, differential changes in DA following pharmacologic challenge in regions other than the NACC alone may be responsible for the addictive liability of a particular drug. Indeed, it has been reported that various addictive drugs can alter DA levels in brain areas other than the NACC including the amygdala, corpus striatum, and frontal cortex, (Hurd, et al., 1997; Dewey, et al., 1997; Di Chiara and Imperato, 1988; Marshall, et al., 1997). Second, neurotransmitters other than DA may play a vital role in the addictive liability of drugs of abuse. For example, a CPP response to cocaine is still maintained in mice that lack the DA and 5-HT transporters (Sora, et al., 1998; Rocha, et al., 1998). Furthermore, it is known that neurotransmitters such as 5-MT, acetylcholine, enkephalins and glutamate, play a role in mediating the effects of addictive drugs, including nicotine (Bardo, 1998; Gardner, 1997). Taken together, these data show that GVG inhibits the effects of cocaine and nicotine through changes in DA in regions other than the NACC. Concomitantly, GVG may be inhibiting other neurotransmitters that either modulate DA directly or are themselves involved in mediating the effects of drugs of addiction. Further studies designed to assess the multiple effects of GVG on other neurotransmitters are ongoing.

Previously, we demonstrated that the ability of GVG to attenuate cocaine-induced increases in NACC DA is completely abolished by pretreating animals with the selective GABAB receptor antagonist SCH 50911 (Bolser et al., 1995), a drug that does not significantly alter DA levels when given alone. Therefore, it can be shown that GVG abolishes the action of nicotine via its increase in GABA levels, which subsequently stimulates GABAB receptors. This is consistent with data indicating that the administration of baclofen, a selective GABAB agonist (Bowery and Pratt, 1992; Kerr et al., 1990), into the VTA significantly attenuates the CPP response in animals produced by systemic morphine (Tsuji et al., 1995). Furthermore, systemic administration of baclofen attenuates cocaine self-administration on a progressive ratio and discrete trials schedule (Roberts et al., 1996, 1997).

It can be argued that GVG attenuates the pharmacologic and behavioral actions of nicotine simply by altering the amount that effectively enters the brain either by changing blood brain barrier permeability or by increasing the systemic rate of metabolism of nicotine. This possibility is unlikely for a number of reasons. First, GVG had no effect on the blood brain barrier transport of $^{11}$C-cocaine, an alkaloid previously shown to increase NACC DA, in both the rodent or primate brain. Second, GVG is excreted primarily in the unchanged form by the kidneys (Grant and Heel, 1991; Porter and Meldrum, 1998), whereas nicotine is metabolized by enzymes in the liver. Finally, GVG does not interact with the hepatic microsomal enzymes (Grant and Heel, 1991; Porter and Meldrum, 1998) and thus would not induce or inhibit these enzymes.

The size of the NACC is well below the resolution of our tomograph making its specific analysis outside the capabilities of this technique. Therefore, our analysis included the corpus striatum, bilaterally and the cerebellum. Marshall et al. (1995) have demonstrated that nicotine increased DA equally in both the NACC and the corpus striatum, while our own microdialysis data demonstrates that GVG decreases DA concentrations equally in both regions as well (Dewey, et al., 1997). These primate data further support the use of this imaging technique to evaluate the functional consequences of pharmacologic challenges in the intact living brain.

Furthermore, this medical imaging technique provides a unique window into the interactions that have been shown to exist between functionally-linked neurotransmitters in both the primate and human brain.

Combined with an exhaustive literature supporting the fundamental principle that neurotransmitters interact in both functionally-specific and regionally specific neuroanatomic foci, it is becoming increasingly clear that new treatment strategies for brain disorders (including addictions to cocaine, nicotine, heroin, methamphetamine and alcohol) can be implemented with a more global awareness of this fundamental and well-documented principle. While changes in individual neurotransmitter concentrations may indeed underlie the etiology of a specific disorder, it is likely that disease progression and symptom development are linked to compensatory or disease-induced changes in other neurotransmitters functionally-linked to the original target. With this knowledge, we have developed novel treatment strategies specifically designed to alter one or more neurotransmitters by targeting another. Our findings with nicotine, cocaine, methamphetamine, alcohol and GVG represent great utility for treatment of mammals addicted to drugs of abuse.

Example 10

Figure 6:
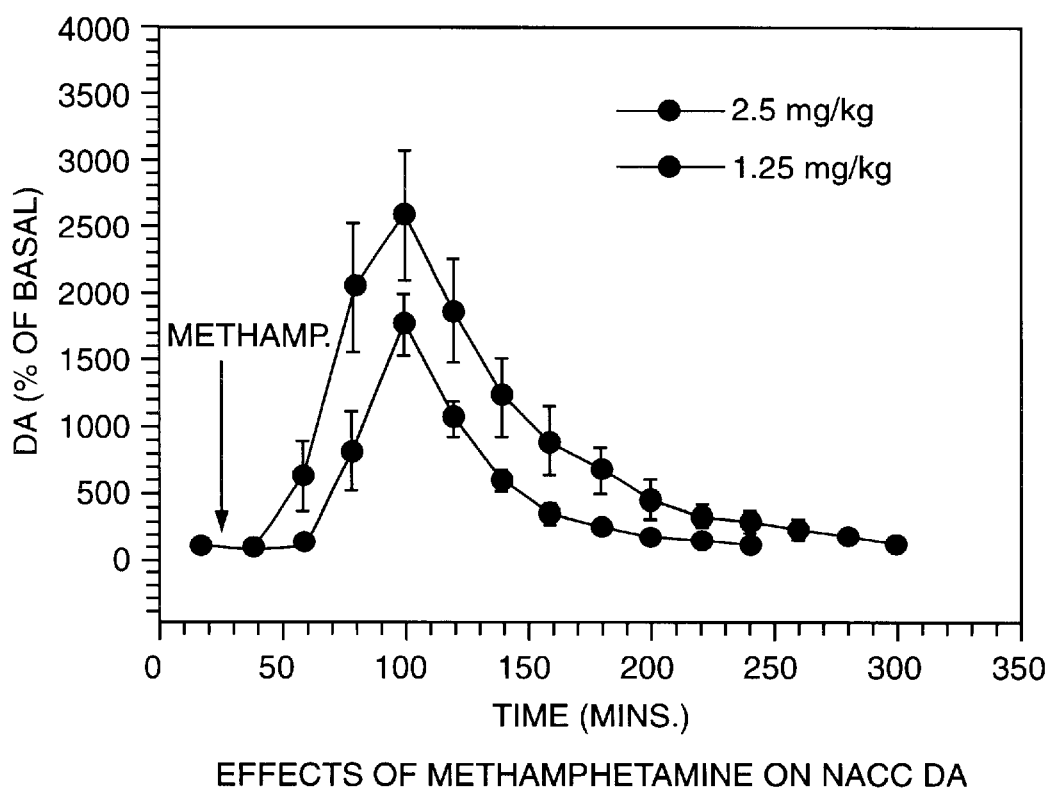
FIG. 6 is a graph illustrating the effects of methamphetamine on extracellular dopamine levels in the nucleus accumbens of freely moving rats.

In this example, the effects of GVG on methamphetamine-induced changes on NACC dopamine concentrations was studied in 6–8 freely moving rats. Methamphetamine at a dose of 1.25 mg/kg i.p. and 2.5 mg/kg i.p. was administered to the animals. It was noted that methamphetamine elevated extracellular DA concentrations in the NACC by approximately 2500% over basal levels, 100 minutes following administration of 2.5 mg/kg and approximately 1500% over basal levels following administration of 1.25 mg/kg (FIG. 6). DA returned to basal levels approximately 200 minutes following administration.

Figure 7:
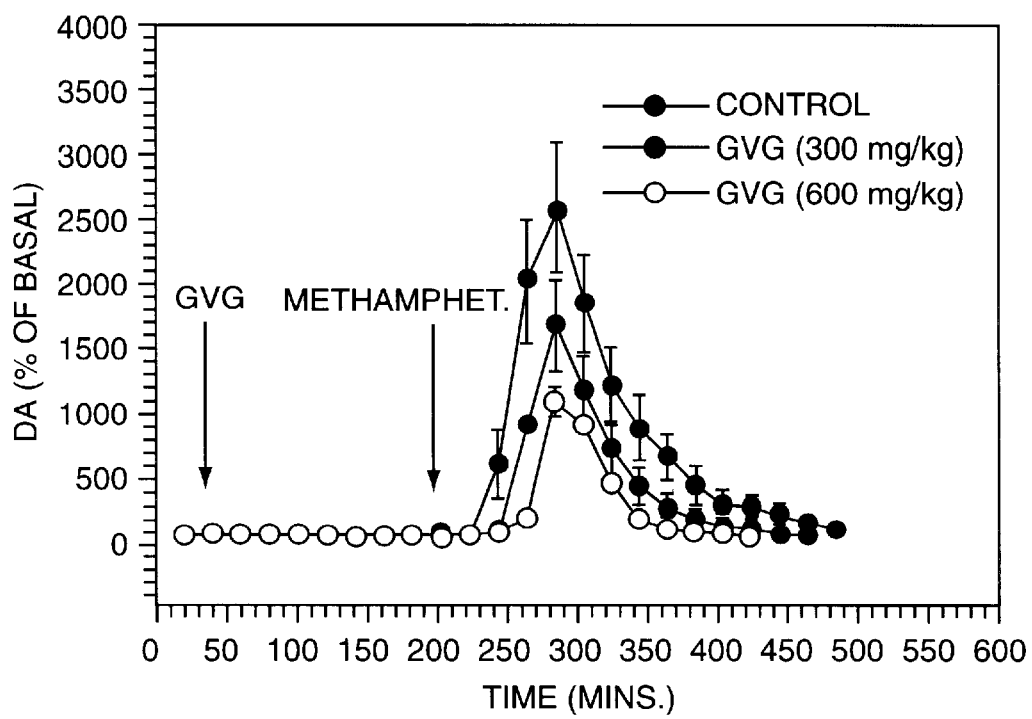
FIG. 7 is a graph illustrating the effects of GVG on methamphetamine induced changes in extracellular dopamine levels in the nucleus accumbens of freely moving rats.

When GVG was administered prior to methamphetamine administration, GVG dose-dependently inhibited the DA increase as shown in FIG. 7. At 300 mg/kg, GVG inhibited increases in DA by approximately 38% and at 600 mg/kg it inhibited increases in DA by approximately 58%. These data demonstrate that GVG inhibits methamphetamine increases in extracellular dopamine concentrations in the NACC.

Thus, it is noted from the above data that the rank order of nicotine, cocaine and methamphetamine to increase NACC DA levels is methamphetamine (2500%)>cocaine (450%)>nicotine (90%) which parallels the rank order of the size of an acute dose of GVG needed to significantly decrease drug-induced increases in NACC DA.

Example 11

In this example, the effects of GVG on ethanol-induced changes on NACC dopamine concentrations was studied in 6–8 freely moving rats. Ethanol at a dose of 1.0 g/kg i.p. was administered to the animals. Ethanol increased elevated extracellular DA concentrations in the NACC by approximately 200% over basal levels at approximately 125 minutes following ethanol administration.

Figure 8:
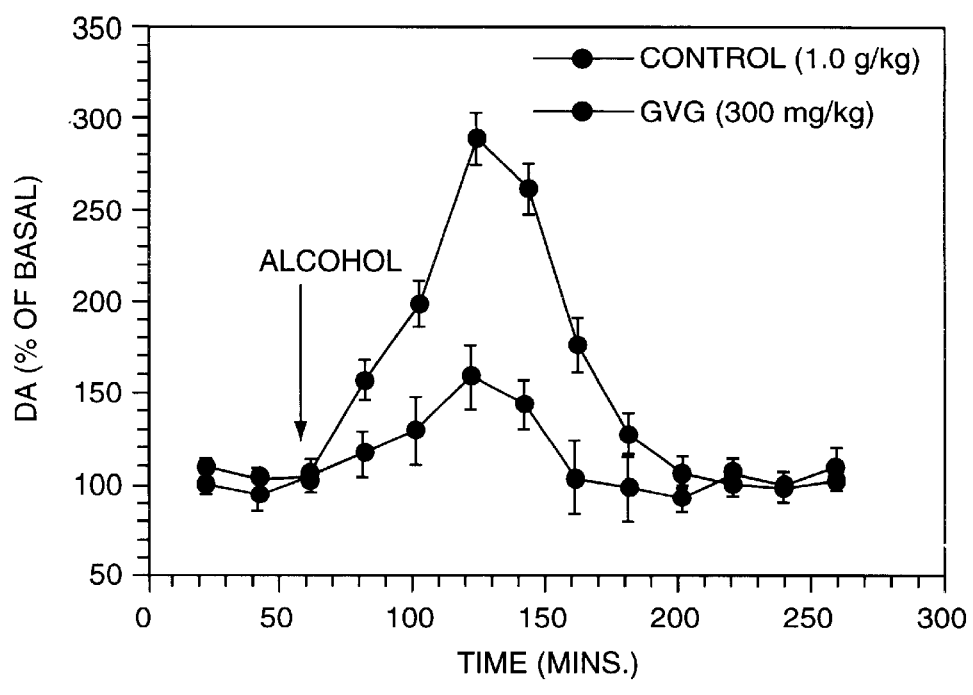
FIG. 8 is a graph illustrating the effects of GVG on alcohol induced changes in extracellular dopamine levels in the nucleus accumbens of freely moving rats.

When GVG was administered at a dose of 300 mg/kg, it inhibited increases in DA by approximately 50% (FIG. 8). Also, at a dose of 100 mg/kg, GVG significantly inhibits, by approximately 40%, alcohol's ability to increase nucleus accumbens dopamine in freely moving rats (data not shown). These data demonstrate that GVG inhibits ethanol increases in extracellular dopamine concentrations in the NACC.

The above studies demonstrate that drugs that selectively target the GABAergic system can be beneficial for the treatment of drugs of abuse, such as psychostimulants, narcotic analgesics, alcohols and nicotine or combinations thereof More specifically, GVG-induced GABA-T inhibition, which produces an increase in extracellular brain GABA levels, represents an effective drug and novel strategy for the treatment of cocaine, nicotine, methamphetamine and ethanol addiction.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

REFERENCES

The following publications, mentioned in the foregoing specification, are incorporated herein by reference as if set forth in full for all they disclose.

Bardo, M. T. (1998) Neuropharmacological mechanism of drug reward: beyond dopamine in the nucleus accumbens. Crit. Rev. Neurobiol., 12: 37–67.

Bolser, D. C., Blythin, D. J., Chapman, R. W., Egan, R. W., Hey, J. A., Rizzo, C., Kuo S.-C., Kreutner, W. (1995). The pharmacology of SCH 5091 1: A novel, orally-active GABA-B receptor antagonist. J. Pharmacol. Exp. Ther., 274: 1393–1398.

Bowery, N. G., Pratt, G. D. (1992) GABAB receptors as targets for drug action Arzneim. Forsch., 42: 215–223.

Brazell, M. P., Mitchell, S. N., Joseph, M. H., Gray, J. A. (1990) Acute administration of nictoine increases the in vivo extracellular levels of dopamine, 3,4-dihydroxyphenylacetic acid and ascorbic acid preferentially in the nucleus accumbens of the rat: Comparison with caudateputamen. Neuropharmacology, 29: 1177–1185.

Chesselet, M.-F. (1984) Presynaptic regulation of neurotransmitter release in the brain: Facts and hypothesis. Neuroscience, 12: 347–375.

Childress, A. R., McLellan, A. T., O'Brien, C. P. (1988). The role of conditioning factors in the development of drug dependence. Psychiatr. Clin. North Amer., 9: 413–426.

Childress, A. R., McLellan, A. T., Ehrman, R. N., O'Brien, C. P. (1986a) Extinction of conditioned responses in abstinent cocaine or opioid users. NIDA Res. Monogr., 76: 189–195.

Childress, A. R., McLellan, A. T., Ehrman, R. N., O'Brien, C. P. (1986b) Classically conditioned responses in abstinent cocaine or opioid users. NIDA Res. Monogr., 76: 24–43).

Clarke, P. B. S., Fibiger, H. C. (1987) Apparent absence of nicotine-induced conditioned place preference. Psychopharmacology, 92: 84–88.

Clarke, P. B. S., Fu, D. S., Jakubovic, A., Fibiger, H. C. (1988) Evidence that mesolimbic dopaminergic activation underlies the locomotor stimulant action of nicotine in animals. J. Pharmacol. Exp. Ther., 246: 701–708.

Damsma, G., Day, J., Fibiger, H. C. (1989) Lack of tolerance to nicotine-induced dopamine release in the nucleus accumbens. Eur. J. Pharmacol., 168: 363–368.

Dewey, S. L., Chaurasia, C. S., Chen, C., Volkow, N. D., Clarkson F. A., Porter, S. P., Straughter-Moore, R. M., Alexoff, D. L., Tedeschi, D., Russo, N. B., Fowler, J. S. and Brodie, J. D. GABAergic attenuation of cocaine-induced dopamine release and locomotor activity. Synapse 25: 393–398, 1997.

Dewey, S. L., Morgan, A. E., Ashby, Jr., C. R., Horan, B., Gardner, E. L., Logan, J., Volkow,. N. D., Fowler, J. S., Kushner, S. A., Brodie, J. D. (1998) A novel strategy for the treatment of cocaine addiction. Synapse, 30: 119–129.

Dewey, S. L., Smith, G. S., Logan, J., Brodie, J. D., Yu, D-W., Ferrieri, R. A., King, P. T., MacGregor, R. R., Martin, T. P., Wolf, A. P., Volkow, N. D., Fowler, J. S. GABAergic inhibition of endogenous dopamine release measured in vivo with 11C-raclopride and positron emission tomography. J. Neuroscience 12,3773–3780, 1992.

Dewey, S. L., Smith, G. S., Logan, J., Brodie, J. D., Fowler, J. S., Wolf, A. P. Striatal binding of the PET ligand 11C-raclopride is altered by drugs that modify synaptic dopamine levels. Synapse 13, 350–356, (1993).

Dewey, S. L., Smith, G. S., Logan, J., Simkowitz, P., Brodie, J. D., Volkow, N. D., Fowler, J. S., Wolf, A. P. (1993) Effects of central cholinergic blockade on striatal dopamine release measured with positron emission tomography (PET) in normal human subjects. Proc. Natl. Acad. Sci., 90: 11816–11820.

Di Chiara, G., Imperato, A. (1988) Drugs abused by humans preferentially increase synaptic dopamine concentrations in the mesolimbic system of freely moving animals. Proc. Natl. Acad. Sci. USA, 85: 5274–5278.

Ehrman, R. N., Robbins, S. J., Childress, A. R., O Brien, C. P. (1992) Conditioned responses to cocaine-related stimuli in cocaine abuse patients. Psychopharmacology, 107: 523–529.

Fudala, P. J., Iwamoto, E. T. (1986) Further studies on nicotine-induced conditioned place preference. Pharmacol. Biochem. Behav., 25: 1041–1049.

Fudala, P. J., Teoh, K. W., Iwamoto, E. T. (1985) Pharmacologic characterization of nicotineinduced conditioned place preference. Pharmacol. Biochem. Behav., 22: 237–241.

Gardner, E. L. (1997) Brain reward mechanisms in Substance Abuse: A Comprehensiove Textbook, 3rd edn., eds. Lowinson, J. H., Ruiz, P., Millmna, R. B. & Langrod, J. G., 51–85 (Williams and Wilkins, Baltimore, Md., 1997).

Grant, S. M. and Heel, R. C. Vigabatrin: A review of its pharmacodynamic and pharmacokinetic properties, and therapeutic potential in epilepsy and disorders of motor control. Drugs, 41:889–926, 1991.

Henningfield, J. E. (1995) Nicotine medications for smoking cessation. New Eng. J. Med., 333: 1196–1203. 26

Henningfield, J. E., Goldberg. S. R. (1983) Control of behavior by intravenous nicotine injections in human subjects. Pharmacol. Biochem. Behav., 19: 1021–1026.

Henningfield, J. E., London, E. D., Jaffe, J. H. (1987) nicotine reward: studies of abuse liability and physical dependence potential. In: Brain Reward Systems and Abuse, ed. By J. Engel and L. Oreland, New York, Raven Press, pp. 147–164.

Henningfield, J. E., Miyasato, K., D. R. Jasinski (1983) Cigarette smokers self-administer intravenous nicotine. Pharmacol. Biochem. Behav., 19: 887–890.

Horan, P., Smith, M., Gardner, E. Lepore, M., Ashby, Jr. C. R. (1997) (-)-nicotine produces conditioned place preference in Lewis, but not Fischer 344 animals. Synapse, 26: 93–94.

Hurd, Y. L., McGregor, A., Ponten, M. (1997). In vivo amygdala dopamine levels modulate cocaine self-administration behaviour in the rat: D1 dopamine receptor involvement. Eur. J. Neuroscience, 12: 2541–2548.

Hurt, R. D., Sachs, D. P., Glover, E. D., Offord, K. P., Johnston, J. A., Dale, L. C., Khayrallah, M. A., Schroeder, D. R., Glover, P. N., Sullivan, C. R., Croghan, I. T., Sullivan, P. M. (1997) A comparison of sustained-release bupropion and placebo for smoking cessation. N. Eng. J. Med., 237: 1195–1202.

Imperato, A., Mulas, A., Di Chiara, G. (1986) Nicotine preferentially stimulates dopamine release in the limbic system of the freely moving rat. Eur. J. Pharmacol., 132: 337–338.

Jarvik, M. E., Henningfield, J. E. (1988) Pharmacological treatment of tobacco dependence. Pharmacol. Biochem. Behav., 30: 279–294.

Jung, M. J., Lippert, B., Metcalf, B. W., Bohlen, P., Schechter, P. J. (1977) Gamma-Vinyl GABA (4aminohex-5-enoic acid), a new selective irreversible inhibitor of GABA-T: effects on brain GABA metabolism in mice. J. Neurochem., 29: 787–802.

Kerr, D. I. B., Ong, J., Prager, R. H. (1990) GABAB receptor agonists and antagonists. In: GABAB receptors in Mammalian Function, Bowery, N. G., Bittiger, H. and Olpe, H.-R. (eds.) John Wiley and Sons, New York, pp. 29–45.

Kushner, S. A., Dewey, S. L., Kornetsky, C. Comparison of the effects of vigabatrin on cocaine self-administration and food reinforcement. Soc. Neuro. Abstr. 23: 1942 (1997a).

Kushner, S. A., Dewey, S. L., Kometsky, C. The effects of gamma-vinyl GABA on cocaine-induced lowering of brain-stimulation reward thresholds. Psychopharmacology, 133, 383–388, (1997b).

Lacey, M. G., Mercuri, N. B. and North, A. N. On the potassium conductance increase activated by GABAB and dopamine D2 receptors in rat substantia nigra neurones. J. Physiol. 401: 437–453, 1988.

Logan, J., Fowler, J. S., Volkow, N. D., Wolf, A. P., Dewey, S. L., Schlyer, D. J., MacGregor, R. R., Hitzemann, R., Bendriem, B., Gatley, S. J., Christman, D. R. (1990) Graphical analysis of reversible radioligand binding from time activity measurements applied to [N-$^{11}$C-methyl]-(-)-cocaine PET studies in human subjects. J. Cereb. Blood Flow and Metab., 10: 740–747.

Marshall, D. L., Redfern, P. H., Wonnacott, S. (1997) Presynaptic nicotinic modulation of dopamine release in the three ascending pathways studied by in vivo microdialysis: Comparison of naive and chronic nicotine-treated rats. J. Neurochem., 68: 1511–1519.

Morgan, A. E., Dewey, S. L. Effects of pharmacologic increases in brain GABA levels on cocaine-induced changes in extracellular dopamine. Synapse 28, 60–65 (1998).

Nisell, M., Nomikos, G. G., Svensson, T. H. (1994a) Systemic nicotine-induced dopamine release in the rat nucleus accumbens is regulated by nicotinic receptors in the ventral segmental area. Synapse, 16: 36–44.

Nisell, M., Nomikos, G. G., Svensson, T. H. (1994b). Infusion of nicotine in the ventral segmental area or the nucleus accumbens differentially affects accumbal dopamine release. Pharmacol. Toxicol., 75: 348–352.

Nisell, M., Nomikos, G. G., Svensson, T. H. (1995) Nicotine dependence, midbrain dopamine systems and psychiatric disorders. Pharmacol. Toxicol., 76: 157–162.

N. R., Van der Kooy, G. F. & Wenger, J. R. Cholecystokinin produces conditioned place-aversion, not place-preferences, in food-deprived rats: evidence against involvement in satiety. Life Sci. 32, 2087–2093, (1989).

O'Brien, C. P., Childress, A. R., McLellan, A. T., Ehrman, R. (1992) A learning model of addiction,. In: Addictive States, O'Brien, C. P. and Jaffe, J. H., (eds), Raven Press, New York, pp. 157177.

Pontieri, F. E., Tanda, G., Orzi, F., Di Chiara, G. (1997) Effects of nicotine on the nucleus accumbens and similarity to those of addictive drugs. Nature, 382: 255–257.

Porter, R. J., Meldrum, B. S. (1998) Antiepileptic drugs. In: Basic and Clinical Pharmacology, ed. by Katzung, B.G., Appelton and Lange, Stamford, Conn., pp. 386–408.

Roberts, D. C., Andrews, M. M. (1997) Baclofen suppression of cocaine self-administration: demonstration using a duscrete trials procedure. Psychopharmacology, 131: 271–277.

Roberts, D. C., Andrews, M. M., Vickers, G. J. (1996) Baclofen attenuates the reinforcing effects of cocaine in animals. Neuropsychopharmacology, 15: 417–423.

Rocha, B. A., Scearce-Levie, K., Lucas, J. J., Hiroi, N., Castanon, N., Crabbe, J. C., Nestler, E. J., Hen, R. (1998). Increased vulnerability to cocaine in mice lacking the serotonin-1B receptor. Nature Neuroscience, 393: 175–178.

Seeman, P., Guan, H. C., Niznik, H. B. (1989) Endogenous dopamine lowers the dopamine D2 receptor density as measured by [3H]raclopride: implications for positron emission tomography of the human brain. Synapse, 3: 96–97.

Sora, I., Wichems, S. I., Takahashi, C., Li, X.F., Zeng, Z., Revay, R., Lesch, K. P., Murphy, D. L., Uhl, D. R. (1998) cocaine reward models: conditioned place preference can be established in dopamine- and serotonin-transporter knockout mice. Proc. NatI. Acad. Sci., U.S.A., 95: 7699–7704.

Takada, K., Yanagita, T. (1997) Drug dependence study on vigabatrin in rhesus monkeys and animals. Arzneim-Forsch Drug Res.47: 1087–1095.

Tsuji M, Nakagawa Y, Ishibashi Y, Yoshii T, Takashima T, Shimada M, Suzuki T. (1995) Activation of ventral segmental GABAB receptors inhibits morphinein-duced place preference in animals. Eur. J. Pharmacol., 313: 169–173.

Valentine, J. D., Hokanson, J. S., Matta, S. G., Sharp, B. M. (1997) Self-administration in animals allowed unlimited access to nicotine. Psychopharmacology, 133: 300–304.

Van Der Kooy, K. (1987). In Methods of Assessing the Properties of Abused Drugs, M. A. Bozarth, Ed., Springer-Verlag, New York, pp. 229–241.

Volkow, N. D., Wang, G. J., Fowler, J. S., Logan, J., Schlyer, D., Hitzemann, R., Liberman, J., Angrist, B., Pappas, N., MacGregor, R., Burr, G., Cooper, T., Wolf, A. P. Imaging endogenous dopamine competition with [11C]raclopride in the human brain. Synapse, 16, 255–262 (1994).

Wikler, A. (1965) Conditioning factors in opiate addiction and relapse. In: Narcotics, Kassenbaum, G. G. and Wilner, D. I. (eds), McGraw-Hill, New York, pp. 85–100.

What is claimed is:

1. A method for changing addiction-related behavior of a primate suffering from addiction to a drug of abuse selected from the group consisting of methamphetamine, morphine and heroin which comprises administering to a primate a composition consisting of gamma vinylGABA (GVG) or a pharmaceutically acceptable salt thereof, and, optionally, incorporating pharmaceutically acceptable excipients, diluents and carriers, wherein said administration is in an amount sufficient to diminish, inhibit or eliminate behavior associated with craving of said drug of abuse.

2. The method of claim 1, wherein said elimination of behavior associated with craving of drugs of abuse occurs in the absence of an aversive response or appetitive response to GVG.

3. The method of claim 1, wherein said composition contains GVG in an amount of about 100 mg/kg to about 300 mg/kg.

4. The method of claim 1, wherein said composition contains GVG in an amount from about 150 mg/kg to about 300 mg/kg.

5. The method of claim 1, wherein said addiction related behavior is conditioned place preference.

6. A method for changing addiction-related behavior of a primate suffering from addiction to a drug of abuse selected from the group consisting of methamphetamine, morphine and heroin which comprises administering to a primate a composition consisting of gamma vinylGABA (GVG) or a pharmaceutically acceptable salt thereof, and, optionally, incorporating pharmaceutically acceptable excipients, diluents and carriers, wherein said administration is in an amount sufficient to attenuate the rewarding/incentive effects of said drug of abuse in the absence of altering rewarding/incentive effects food in said primate.

7. The method of claim 6, wherein the rewarding/incentive effects of drugs of abuse is attenuated in the absence of an alteration in the locomotor function of said primate.

8. A method for changing addiction-related behavior of a mammal suffering from addiction to a drug of abuse selected from the group consisting of methamphetamine, morphine and heroin which comprises administering to the mammal a composition consisting of gamma vinylGABA (GVG) or a pharmaceutically acceptable salt thereof, and, optionally, incorporating pharmaceutically acceptable excipients, diluents and carriers, wherein said administration is sufficient to diminish, inhibit or eliminate behavior associated with craving or use of said drug of abuse.

9. The method of claim 8, wherein said elimination of behavior associated with craving of drugs of abuse occurs in the absence of an aversive response or appetitive response to GVG.

10. The method of claim 8, wherein GVG is administered in an amount of about 15 mg/kg to about 600 mg/kg.

11. The method of claim 8, wherein said addiction related behavior is conditioned place preference.

12. A method for changing addiction-related behavior of a mammal suffer from addiction to a drug of abuse selected from the group consisting of methamphetamine, morphine and heroin which comprises administering to the mammal a composition consisting of gamma vinylGABA (GVG) or a pharmaceutically acceptable salt thereof, and, optionally, incorporating pharmaceutically acceptable excipients, diluents and carriers, wherein said administration attenuates the rewarding, incenitive effects of said drug of abuse in the absence of altering rewarding/incentive effects of food in said mammal.

13. The method of claim 12, wherein the rewarding/incentive effects of drugs of abuse is attenuated in the absence of an alteration in the locomotor function of said mammal.

14. A method of ameliorating effects of addiction to methamphetamine, morphine or heroin which comprises administering to a mammal a composition consisting of gamma vinylGABA (GVG) or a pharmaceutically acceptable salt thereof, and, optionally, incorporating pharmaceutically acceptable excipients, diluents and carriers, wherein said administration is in an amount sufficient to reduce methamphetamine, morphine or heroin dependency characteristics.

15. The method of claim 14, wherein GVG is administered in an amount from about 15 mg/kg to about 600 mg/kg.

16. The method of claim 14, wherein said dependency characteristics are reduced in the absence of an aversive response or appetitive response to GVG.

17. The method of claim 14, wherein said dependency characteristics are reduced in the absence of an alteration in the locomotor function of said mammal.

18. A method for changing addiction-related behavior of a mammal suffering from addiction to drugs of abuse which comprises administer ing to the mammal an effective amount of a composition consisting of a racemic mixture of gamma vinylGABA (GVG) or an enanotiomer of GVG, and, optionally, incorporating pharmaceutically acceptable excipients, diluents, and carriers, wherein the effective amount is sufficient to diminish, inhibit or eliminate behavior associated with craving or use of drugs of abuse.

19. The method of claim 18, wherein said elimination of behavior associated with craving of drugs of abuse occurs in the absence of an aversive response or appetitive response to GVG.

20. The method of claim 18, wherein said drug of abuse is selected from the group consisting of psychostimulants, narcotic analgesics, or nicotine.

21. The method of claim 18, wherein said drug of abuse is selected from the group consisting of cocaine, nicotine, methamphetamine, morphine, and heroin.

22. The method of claim 18, wherein GVG is administered in an amount of about 15 mg/kg to about 600 mg/kg.

23. The method of claim 18, wherein said addiction related behavior is conditioned place preference.

24. A method for changing addiction-related behavior of a mammal suffering from addiction to drugs of abuse which comprises administering to the mammal an effective amount of a composition consisting of a racemic mixture of gamma vinylGABA (GVG) or an enanotiomer of GVG, and, optionally, incorporating pharmaceutically acceptable excipients, diluents, and carriers, wherein the effective amount attenuates the rewarding/incentive effects of drugs of abuse selected from the group consisting of psychostimulants, narcotic analgesics, and nicotine in the absence of altering rewarding/incentive effects of food in said mammal.

25. The method of claim 24, wherein the rewarding/incentive effects of drugs of abuse is attenuated in the absence of an alteration in the locomotor function of said mammal.

26. A method of ameliorating effects of psychostimulant, narcotic analgesic, or nicotine addiction which comprises administering to a mammal an effective amount of a compound consisting of a racemic mixture of gamma vinyl-GABA (GVG) or an enantiomer of GVG, and, optionally, incorporating pharmaceutically acceptable excipients, diluents, and carriers, wherein the effective amount is sufficient to reduce psychostimulant, narcotic analgesic, or nicotine dependency characteristics.

27. The method of claim 26, wherein GVG is administered in an amount from about 15 mg/kg to about 600 mg/kg.

28. The method of claim 26, wherein said psychostimulant, narcotic analgesic, or nicotine dependency characteristics are reduced in the absence of an aversive response or appetitive response to GVG.

29. The method of claim 26, wherein said psychostimulant, narcotic analgesic, or nicotine dependency characteristics are reduced in the absence of an alteration in the locomotor function of said mammal.

30. A method of changing addiction-related behavior of a mammal suffering from addiction to cocaine, nicotine, methamphetamine, morphine, or heroin which comprises administering to the mammal a compound consisting of enantiomer S(+)-gamma-vinylGABA, or a pharmaceutically acceptable salt thereof, and, optionally, incorporating pharmaceutically acceptable excipients, diluents, and carriers, in an amount sufficient to diminish, inhibit or eliminate behavior associated with addiction.

31. A method of changing addiction-related behavior of a mammal suffering from addiction to cocaine, nicotine, methamphetamine, morphine, or heroin which comprises administering to the mammal a compound consisting of enanotiomer R(−)-gamma-vinylGABA, or a pharmaceutically acceptable salt thereof, and, optionally, incorporating pharmaceutically acceptable excipients, diluents, and carriers, in an amount sufficient to diminish, inhibit or eliminate behavior associated with addiction.

* * * * *